United States Patent

Rathinasabapathi et al.

(10) Patent No.: US 7,202,084 B2
(45) Date of Patent: Apr. 10, 2007

(54) BETA-ALANINE N-METHYLTRANSFERASE

(75) Inventors: Bala Rathinasabapathi, Gainesville, FL (US); Suresh Badu Raman, Gainesville, FL (US)

(73) Assignee: University of Florida Research Foundation, Inc., Gainesville, FL (US)

( * ) Notice: Subject to any disclaimer, the term of this patent is extended or adjusted under 35 U.S.C. 154(b) by 121 days.

(21) Appl. No.: 10/213,473

(22) Filed: Aug. 6, 2002

(65) Prior Publication Data

US 2003/0104598 A1 Jun. 5, 2003

Related U.S. Application Data

(63) Continuation-in-part of application No. 10/132,100, filed on Apr. 24, 2002.

(60) Provisional application No. 60/286,162, filed on Apr. 24, 2001.

(51) Int. Cl.
*C12N 15/82* (2006.01)
*C12N 15/29* (2006.01)
*A01H 5/00* (2006.01)

(52) U.S. Cl. ................ 435/419; 435/252.3; 435/320.1; 536/23.6; 800/298

(58) Field of Classification Search ............. 435/252.3, 435/320.1, 419, 468; 536/23.6; 800/289, 800/298
See application file for complete search history.

(56) References Cited

OTHER PUBLICATIONS

Broun P et al. Catalytic plasticity of fatty acid modification enzymes underlying chemical diversity of plant lipids. Science. Nov. 13, 1998;282(5392):1315-7.*

Rathinasabapathi B et al. Metabolic engineering of glycine betaine synthesis: plant betaine aldehyde dehydrogenases lacking typical transit peptides are targeted to tobacco chloroplasts where they confer betaine aldehyde . . . Planta. 1994;193(2):155-62.*

Nuccio ML et al.The endogenous choline supply limits glycine betaine synthesis in transgenic tobacco expressing choline monooxygenase. Plant J. Nov. 1998;16(4):487-96.*

Hu et al. A bifunctional enzyme (delta 1-pyrroline-5-carboxylate synthetase) catalyzes the first two steps in proline biosynthesis in plants. Proc Natl Acad Sci U S A. Oct. 1, 1992;89(19):9354-8.*

Tamura T et al. Osmotic stress tolerance of transgenic tobacco expressing a gene encoding a membrane-located receptor-like protein from tobacco plants. Plant Physiol. Feb. 2003;131(2):454-62.*

Hu CA et al. A bifunctional enzyme (delta 1-pyrroline-5-carboxylate synthetase) catalyzes the first two steps in proline biosynthesis in plants. Proc Natl Acad Sci U S A. Oct. 1, 1992;89(19):9354-8.*

Van Camp W. et al. Enhancement of oxidative stress tolerance in transgenic tobacco plants overproducing Fe-superoxide dismutase in chloroplasts. Plant Physiol. Dec. 1996;112(4):1703-14.*

* cited by examiner

*Primary Examiner*—Cynthia Collins
(74) *Attorney, Agent, or Firm*—Akerman Senterfitt; Nicholas A. Zachariades

(57) ABSTRACT

A β-alanine NMTase was isolated from *Lumonium latifolium*. The purified enzyme catalyzes the N-methylation of β-alanine betaine, has an isoelectric point of about 5.15 and an apparent molecular weight of about 43 kilodaltons. A full-length cDNA encoding the NMTase was cloned by screening a *L. latifolium* cDNA library and was sequenced. Expression of the cDNA in transgenic, non-*L. latifolium* plants resulted in modulation of resistance to stress in the plants.

8 Claims, 7 Drawing Sheets

A

GTGCTAAGCCAGACACACACACGCAGAGTGAGTGAGTCAGTCAATTGGTG
ATAGACAGTTCCAGTTCCAGTCCCAGTTATCACCAACCAACCAACCAAGC
AAGCAACCAAGCGAGAAAAATGGCGAACCACTCCTCAGCTGCAGCCATGG
TGGTCGACGAGACTTCAGAGGCCCGAAACAATGCGAGGCTAAAGATCATC
GAACTCGCGAACTTAATCAGTGTTCCTATGTCCCTTACTGCCATCGTCCG
CCTGAAGGTGCCTGAGGCTATCTGGTCTAATGGTTCCAACACCCCGGTCT
CTGCCGCTGAGATCCTCAGTCGTCTTCCTGATGCCCCGCTACCGCCGAT
GCGGAGAATCTCCAGCGTCTTCTCCGTGTACTGACTAGTTTTGGCGTTTT
CTCGGAACACCTTGACACCACCAGTTCTAGTTCATCATCTACTTCGGAAC
GGAGGTACTGTTTGACGGAGGTAGGACAGACCCTGGTATCATTTGATGAG
AGCTGTCCATCTCACGGTGCATACGTTCTACAACACCACCAGGAGACGCT
TTTGAAAGCTTGGCCATTTCTTCACACAGCAATTCTAGACGCGAGTACTG
AGCCATTTGCAAGGGTGAATGGTGAGCCAGCTTACCAGTACTACGGGAAG
AATGACGAGTTGAACAAGAATATGCAGTATGCTATGTCAGGGGTATCAGT
GCCTTATATGAAAGCCTTGTTAGGAAGTGGGTACGATGGGTTTGAGGGAG
TAAAAACATTGGTAGATGTTGGTGGGAGTTCAGGGGATTGTTTGAGGATG
ATTATAAACAAGTATAAGGATATTCCAAAAGCCATTAACTTTGATTTACC
TGAGGTTGTGGCGAAAGCGCCTAAGATCCCAGGTATTACCCATGTGGGAG
GAAACATGTTCGAATCGGTTCCTTCGGGTGATGCTATATTTGTGAAGTGG
GTGCTGACGTGTTTCACAGATGAAGAGGTGATCACACTTATGCGCAACTG
TAACAAGGCGTTGCCAGTGGGAGGAAAACTAATATGCTCAGAACCCACGT
TGCCTGAAAACTCGGATGAAAGTCATAGGACTCGTGCTTTGCTTGTAGCC
GACATCTTTATCATGACTACTTACAGGGCAAAGGGAAAGCACAGGACAGA
GGAAGAATACAGACAACTCGGTCTCTTAGCCGGATTCCCCAAATTCCGAG
TTATCCATGTCGACTATTTCTTCCCCGTGGTAGAGTTCCAGAAGTGAATG
TCCATCATCATCATGAGGCCCGCCCGCCCGCCCGCCCGACTATCTCTTTT
TATTATTTTTTTGTGTTTGTGTGTGTCTGTCTGTCCGTCTGTTTAATTT
TAATTTGGGATCAGGTTATAAATAATTTTCTCAGTTGATGATTAAAAAAA
AAAAAAAAAAAAAA

B

MANHSSAAAMVVDETSEARNNARLKIIELANLISVPMSLT
AIVRLKVPEAIWSNGSNTPVSAAEILSRLPDAPATADAEN
LQRLLRVLTSFGVFSEHLDTTSSSSSTSERRYCLTEVGQT
LVSFDESCPSHGAYVLQHHQETLLKAWPFLH<u>TAILDASTE</u>
PFARVNGEPAYQYYGKNDELKNM̲QYAM̲SGVSVPYMKA̲
<u>LLGSGYDGFEGVKTLVDVGGSSGDCLRM̲IINKYKDIPKAI</u>
<u>NFDLPEVVA̲KAPKIPGITHVGGNM̲FESVPSGDAIFVKWV</u>
LTCFTDEEVITLM̲RNCNKALPVGGKLICSEPTLPENSDES
HRTRALLVADIFIM̲TTYRAKGK<u>HRTEEEYRQLGLLA</u>GFPK
<u>FRVIHVDYFFPV̲VEFQK</u>

BETA-ALANINE N-METHYLTRANSFERASE

CROSS REFERENCE TO RELATED APPLICATION

The present application is a continuation-in-part of U.S. application Ser. No. 10/132,100, filed Apr. 24, 2002 which claims the priority of U.S. provisional patent application No. 60/286,162, filed Apr. 24, 2001, and entitled "N-Methyltransferase Involved In Beta-alanine Betaine Synthesis."

STATEMENT AS TO FEDERALLY SPONSORED RESEARCH

The invention was made with U.S. government support under grant numbers NRICGP 2001-35318-10947 and HOS3807, both awarded by the U.S. Department of Agriculture. The U.S. government may have certain rights in the invention.

FIELD OF THE INVENTION

The invention relates generally to the fields of biology, botany, and agricultural sciences. More particularly, the invention relates to the cloning, purification, and characterization of an N-methyltransferase from *Limonium latifolium*, and to methods and compositions for modulating a plant's resistance to environmental stress.

BACKGROUND

Many plants, bacteria and marine algae accumulate quaternary ammonium compounds (QACs) in response to abiotic stresses such as drought and salinity. Gorham J (1991) Betaines in higher plants—biosynthesis and role in stress metabolism. In R M Wallsgrove, ed., Amino acids and their derivatives in higher plants. Cambridge University Press, Cambridge, pp 173–203. QACs can accumulate to high concentrations to increase the osmotic pressure of the cytoplasm without perturbing metabolism. Yancey P H (1994) Compatible and counteracting solutes. In K. Strange, ed., Cellular and molecular physiology of cell volume regulation. CRC Press, Boca Raton, Fla. pp 81–109 They also stabilize enzymes and membranes. Id. The synthetic pathway to glycine betaine, the most common QAC, has therefore been the target of recent metabolic engineering efforts to improve plant stress tolerance. McNeil et al., Plant Physiol 120:945–949, 1999; Rathinasabapathi, Ann Bot 86:709–716, 2000; Sakamoto and Murata, J Exp Bot 51:81–88, 2000. However, these efforts have met with only limited success due to metabolic constraints on the availability of the precursor choline. Hayashi et al., Plant J 12:133–142, 1997; Nuccio et al., Plant J 12:133–142, 1998; Huang et al., Plant Physiol 122:747–756, 2000.

Most members of the highly stress-tolerant plant family Plumbaginaceae accumulate β-alanine betaine instead of glycine betaine. Hanson et al., Plant Physiol 97:1199–1205, 1991; Hanson et al., Proc Natl Acad Sci USA 91:306–310, 1994. It was proposed that β-alanine betaine is a more suitable osmoprotectant than glycine betaine under saline hypoxic conditions since the first step in glycine betaine synthesis requires molecular oxygen. Id. Further, β-alanine betaine accumulation was proposed to be an evolutionary strategy to avoid metabolic limitations for choline (Hanson et al., Proc Natl Acad Sci USA 91:306–310, 1994) since β-alanine betaine is synthesized from the ubiquitous primary metabolite β-alanine.

To further investigate the synthesis and biological significance of β-alanine betaine, radiotracer experiments were conducted. These experiments showed that β-alanine betaine is synthesized by S-adenosyl-L-methionine (AdoMet) dependent N-methylation of β-alanine via N-methyl β-alanine and N,N-dimethyl β-alanine (Rathinasabapathi et al., Physiol Plant 109: 225–231, 2000; FIG. 1). Using a rapid and sensitive radiometric assay, AdoMet dependent N-methyltransferase (NMTase) activities were demonstrated in β-alanine betaine accumulating members of the Plumbaginaceae family (Rathinasabapathi et al., Physiol Plant 109: 225–231, 2000). Heretofore, however, the gene encoding the NMTase was not cloned, and the protein responsible for the NMTase activities was uncharacterized.

SUMMARY

The invention relates to the purification and characterization of an NMTase from *L. latifolium* and the cloning of the gene that encodes the NMTase. The NMTase was purified from *L. latifolium* leaf tissue using a seven-step protocol. Biochemical characterization of the purified enzyme indicated that it had an isoelectric point (pI) of 5.1, and that it was a dimer of 43 kD subunits. Functional studies indicated that the purified enzyme catalyzes all three of the N-methylations involved in the synthesis of β-alanine betaine. Peptide sequencing studies indicated that the purified NMTase shared some sequence similarity to methyltransferases from other organisms. Peptide sequences from purified β-alanine NMTase were used to design degenerate primers for RT-PCR that yielded a 500 bp cDNA clone. A full-length 1414 bp cDNA representing NMTase A was cloned by screening a lambda gt10 *L. latifolium* cDNA library using the 500 bp cDNA clone as a probe. Transgenic tobacco plants expressing *L. latifolium* β-alanine NMTase accumulated β-alanine betaine and exhibited a stress-tolerant phenotype.

Accordingly, a purified nucleic acid which includes a nucleotide sequence that encodes a protein that: (a) shares at least 90% (e.g., 95%, 98%, or 100%) sequence identity with at least 50 (e.g., 100, 500, or more) contiguous amino acids of SEQ ID) NO:29; and (b) has at least one functional activity of a native *Limonium latifolium* NMTase. The nucleotide sequence can also be one that shares at least 65% (e.g., 75%, 85%, 95%, 97%, 99%, or 100%) sequence identity with SEQ ID NO:29.

Also within the invention is a vector that includes a nucleic acid of the invention. In the vector, the nucleic acid can be operably linked to one or more expression control sequences (e.g., a promoter).

In another aspect, the invention features a purified protein that: (a) shares at least 90% (e.g., 95% or 99%) sequence identity with at least 50 contiguous amino acids of SEQ ID NO:29; and (b) has at least one functional activity of a native *Limonium latifolium* NMTase. The purified protein can also be one that shares at least 85% (e.g., 95% or 100%) sequence identity with SEQ ID NO:28.

Additionally within the invention is a cell into which has been introduced a nucleic acid or protein of the invention. In certain embodiments, the cell is a plant cell (e.g., one in a plant).

The invention further includes a purified antibody that specifically binds to the protein of the invention.

A method of modulating stress resistance in a plant cell or seed is included in the invention. This method includes the steps of: (a) providing a plant cell or seed; and (b) introducing into the plant cell or seed a purified nucleic acid or purified protein of the invention.

Unless otherwise defined, all technical terms used herein have the same meaning as commonly understood by one of ordinary skill in the art to which this invention belongs. Definitions of molecular biology terms can be found, for example, in Rieger et al. (1991) Glossary of Genetics: Classical and Molecular, 5th edition, Springer-Verlag: New York; and Lewin, (1994) Genes V, Oxford University Press: New York.

By the term "gene" is meant a nucleic acid molecule that codes for a particular protein, or in certain cases a functional or structural RNA molecule. For example, the NMTase gene encodes the NMTase protein.

As used herein, a "nucleic acid" or a "nucleic acid molecule" means a chain of two or more nucleotides such as RNA (ribonucleic acid) and DNA (deoxyribonucleic acid). A "purified" nucleic acid molecule is one that has been substantially separated or isolated away from other nucleic acid sequences in a cell or organism in which the nucleic acid naturally occurs (e.g., 30, 40, 50, 60, 70, 80, 90, 95, 96, 97, 98, 99, 100% free of contaminants). The term includes, e.g., a recombinant nucleic acid molecule incorporated into a vector, a plasmid, a virus, or a genome of a prokaryote or eukaryote. Examples of purified nucleic acids include cDNAs, fragments of genomic nucleic acids, nucleic acids produced by polymerase chain reaction (PCR), nucleic acids formed by restriction enzyme treatment of genomic nucleic acids, recombinant nucleic acids, and chemically synthesized nucleic acid molecules. A "recombinant" nucleic acid molecule is one made by an artificial combination of two otherwise separated segments of sequence, e.g., by chemical synthesis or by the manipulation of isolated segments of nucleic acids by genetic engineering techniques.

By the terms "NMTase gene," "NMTase polynucleotide," "NMTase nucleic acid", or simply "NMTase" is meant a native NMTase-encoding nucleic acid sequence, e.g., the native *L. latifolium* NMTase cDNA shown in FIG. 7A (SEQ ID NO: 28), genomic sequences from which NMTase cDNA can be transcribed, and/or allelic variants and homologs of the foregoing. The terms encompass double-stranded DNA, single-stranded DNA, and RNA.

The terms "isolated" and "purified," as used herein with respect to an enzyme, refer to a enzymatically active molecule substantially separated from other molecules that are present in a cell or organism in which the enzymatically active molecule naturally occurs. A purified NMTase includes, e.g., a NMTase-containing cell extract that has been subjected to one or more number of chromatographic separations. The terms "isolated" and "purified" as used herein also refer to a molecule produced artificially (i.e., outside the organism in which the molecule naturally occurs) by molecular biological techniques (e.g., recombinant DNA technology) or chemical synthesis (e.g., peptide synthesis).

As used herein, "protein" or "polypeptide" are used synonymously to mean any peptide-linked chain of amino acids, regardless of length or post-translational modification, e.g., glycosylation or phosphorylation. A "purified" polypeptide is one that has been substantially separated or isolated away from other polypeptides in a cell or organism in which the polypeptide naturally occurs (e.g., 30, 40, 50, 60, 70, 80, 90, 95, 96, 97, 98, 99, 100% free of contaminants).

By the terms "NMTase protein" "NMTase polypeptide," or simply "NMTase" is meant an expression product of an NMTase gene such as the protein whose sequence is shown in FIG. 7B (SEQ ID NO:29); or a protein that shares at least 65% (but preferably 75, 80, 85, 90, 95, 96, 97, 98, or 99%) amino acid sequence identity with SEQ ID NO:29 and displays a functional activity of NMTase. A "functional activity" of a protein is any activity associated with the physiological function of the protein. For example, functional activities of NMTase include N-methyltransferase activity, the ability to interact with substrates of the enzyme (e.g., β-alanaine), N-methyl β-alanaine, and N,N-dimethyl β-alanaine), and the ability to impart stress resistance to a plant or plant cell.

When referring to a nucleic acid molecule or polypeptide, the term "native" refers to a naturally-occurring (e.g., a "wild-type") nucleic acid or polypeptide. A "homolog" of a *L. latifolium* NMTase gene is a gene sequence encoding a NMTase polypeptide isolated from a plant other than *L. latifolium*. Similarly, a "homolog" of a native NMTase polypeptide is an expression product of an NMTase homolog.

A "fragment" of an NMTase nucleic acid is a portion of an NMTase nucleic acid that s less than full-length and comprises at least a minimum length capable of hybridizing specifically with a native NMTase nucleic acid under stringent hybridization conditions. The length of such a fragment is preferably at least 15 nucleotides, more preferably at least 20 nucleotides, and most preferably at least 30 nucleotides of a native NMTase nucleic acid sequence. A "fragment" of an NMTase polypeptide is a portion of an NMTase polypeptide that is less than full-length (e.g., a polypeptide consisting of 5, 10, 15, 20, 30, 40, 50, 75, 100 or more amino acids of native NMTase), and preferably retains at least one functional activity of native NMTase.

When referring to hybridization of one nucleic to another, "low stringency conditions" means in 10% formamide, 5× Denhart's solution, 6×SSPE, 0.2% SDS at 42° C., followed by washing in 1×SSPE, 0.2% SDS, at 50° C.; "moderate stringency conditions" means in 50% formamide, 5× Denhart's solution, 5×SSPE, 0.2% SDS at 42° C., followed by washing in 0.2×SSPE, 0.2% SDS, at 65° C.; and "high stringency conditions" means in 50% formamide, 5× Denhart's solution, 5×SSPE, 0.2% SDS at 42° C., followed by washing in 0.1×SSPE, and 0.1% SDS at 65° C. The phrase "stringent hybridization conditions" means low, moderate, or high stringency conditions.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

When referring to mutations in a nucleic acid molecule, "silent" changes are those that substitute one or more base pairs in the nucleotide sequence, but do not change the amino acid sequence of the polypeptide encoded by the sequence. "Conservative" changes are those in which at least one codon in the protein-coding region of the nucleic acid has been changed such that at least one amino acid of the polypeptide encoded by the nucleic acid sequence is substituted with a another amino acid having similar characteristics. Examples of conservative amino acid substitutions are ser for ala, thr, or cys; lys for arg; gln for asn, his, or lys; his for asn; glu for asp or lys; asn for his or gln; asp for glu; pro for gly; leu for ile, phe, met, or val; val for ile or leu; ile for leu, met, or val; arg for lys; met for phe; tyr for phe or trp; thr for ser; trp for tyr; and phe for tyr.

As used herein, the term "vector" refers to a nucleic acid molecule capable of transporting another nucleic acid to which it has been linked. One type of preferred vector is an episome, i.e., a nucleic acid capable of extra-chromosomal replication. Preferred vectors are those capable of autonomous replication and/or expression of nucleic acids to which they are linked. Vectors capable of directing the expression of genes to which they are operatively linked are referred to herein as "expression vectors."

A first nucleic-acid sequence is "operably" linked with a second nucleic-acid sequence when the first nucleic-acid sequence is placed in a functional relationship with the second nucleic-acid sequence. For instance, a promoter is operably linked to a coding sequence if the promoter affects the transcription or expression of the coding sequence. Generally, operably linked nucleic acid sequences are contiguous and, where necessary to join two protein coding regions, in reading frame.

A cell, tissue, or organism into which has been introduced a foreign nucleic acid, such as a recombinant vector, is considered "transformed," "transfected," or "transgenic." A "transgenic" or "transformed" cell or organism (e.g., a plant) also includes progeny of the cell or organism, including progeny produced from a breeding program employing such a "transgenic" cell or organism as a parent in a cross. For example, a plant transgenic for NMTase is one in which NMTase nucleic acid has been introduced.

The term "antibody" means an immunoglobulin or fragment of an immunoglobulin that retains a function of an intact immunoglobulin, e.g., antigen-binding or effector functions. By the term "NMTase-specific antibody" is meant an antibody that binds NMTase (e.g., a protein having the amino acid sequence of SEQ ID NO:29), and displays no substantial binding to other naturally occurring proteins other than those sharing the same antigenic determinants as NMTase. The term includes polyclonal and monoclonal antibodies.

As used herein, "bind," "binds," or "interacts with" means that one molecule recognizes and adheres to a particular second molecule in a sample, but does not substantially recognize or adhere to other structurally unrelated molecules in the sample. Generally, a first molecule that "specifically binds" a second molecule has a binding affinity greater than about $10^5$ to $10^6$ liters/mole for that second molecule.

The term "labeled," with regard to a probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions will control. In addition, the particular embodiments discussed below are illustrative only and not intended to be limiting.

BRIEF DESCRIPTION OF THE DRAWINGS

The above and further advantages of this invention may be better understood by referring to the following description taken in conjunction with the accompanying drawings, in which:

FIG. 7(A) illustrates a full length NMTase cDNA of *L. Latifolium* (SEQ ID NO:28). The first ATG in the open reading frame and the stop codon are bolded. Also illustrated (B) is the *L. Latifolium* NMTase deduced amino acid sequence (SEQ ID NO:29). Underlined sequences match to peptides sequenced from purified NMTase. S-adenosyl L-methionine binding motifs A, B, and C are shown in bold.

DETAILED DESCRIPTION

Figure 1:
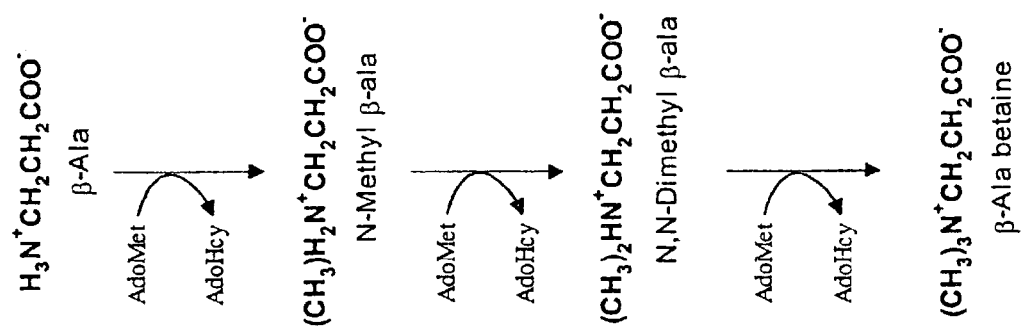
FIG. 1 is a schematic overview of the synthetic pathway to β-alanine betaine. Each downward arrow represents an AdoMet dependent N-methylation step.

The invention provides compositions and methods relating to NMTase, as well as methods and compositions for modulating stress resistance in a plant cell or plant seed, including, in particular, resistance to salinity and hypoxia. For example, according to the invention, stress resistance in a plant cell is modulated by introducing into the cell a nucleic acid encoding a functional β-alanine NMTase. Stress resistance in a plant cell can also be modulated by introducing into the cell a purified β-alanine NMTase. Introduction of the enzyme into a cell can modulate the methylation of substrates such as β-alanine, N-methyl β-alanine, and N,N,-dimethyl β-alanine. Modulation of the methylation events is useful in increasing or reducing stress tolerance in the cell. The cell into which has been introduced a nucleic acid encoding β-alanine NMTase, a purified NMTase or NMTase fragment thereof, is preferably a plant cell, e.g., one other than *L. latifolium*. The plant cell can be one within a plant.

The below described preferred embodiments illustrate adaptations of these compositions and methods. Nonetheless, from the description of these embodiments, other aspects of the invention can be made and/or practiced based on the description provided below.

Biological Methods

Methods involving conventional molecular biology techniques are described herein. Such techniques are generally known in the art and are described in detail in methodology treatises such as Molecular Cloning: A Laboratory Manual, 3rd ed., vol. 1–3, ed. Sambrook et al. (2001) Cold Spring Harbor Laboratory Press, Cold Spring Harbor, N.Y.; and Current Protocols in Molecular Biology, ed. Ausubel et al. (1992) Greene Publishing and Wiley-Interscience, New York (with periodic updates). Various techniques using polymerase chain reaction (PCR) are described, e.g., in Innis et al. (1990) PCR Protocols: A Guide to Methods and Applications, Academic Press: San Diego. PCR-primer pairs can be derived from known sequences by known techniques such as using computer programs intended for that purpose (e.g., Primer, Version 0.5, 1991, Whitehead Institute for Biomedical Research, Cambridge, MA.). Methods for chemical synthesis of nucleic acids are discussed, for example, in Beaucage and Carruthers (1981) Tetra. Letts. 22:1859–1862 and Matteucci et al. (1981) J. Am. Chem. Soc. 103:3185. Chemical synthesis of nucleic acids can be performed, for example, on commercial automated oligonucleotide synthesizers. Immunological methods (e.g., preparation of antigen-specific antibodies, immunoprecipitation, and immunoblotting) are described, e.g., in Current Protocols in Immunology, ed. Coligan et al. (1991) John Wiley & Sons, New York; and Methods of Immunological Analysis, ed. Masseyeffet al. (1992) John Wiley & Sons, New York.

Nucleic Acids Encoding NMTase

The invention provides a purified nucleic acid (polynucleotide) that encodes a polypeptide having the amino acid sequence of FIG. 7B (SEQ ID NO:29). A preferred nucleic acid molecule of the invention is the native NMTase polynucleotide shown in FIG. 7A (SEQ ID NO:28). As native NMTase polynucleotide was discovered in a *L. latifolium* cDNA library, nucleic acid molecules encoding a polypeptide of the present invention can be obtained from *L. latifolium* plants.

Nucleic acid molecules of the present invention may be in the form of RNA or in the form of DNA (e.g., cDNA, genomic DNA, and synthetic DNA). The DNA may be double-stranded or single-stranded, and if single-stranded may be the coding (sense) strand or non-coding (anti-sense) strand. The coding sequence which encodes native NMTase may be identical to the nucleotide sequence shown in FIG. 7A (SEQ ID NO:28). It may also be a different coding sequence which, as a result of the redundancy or degeneracy of the genetic code, encodes the same polypeptide as the polynucleotide of SEQ ID NO:28. Other nucleic acid molecules within the invention are variants of NMTase such as those that encode fragments, analogs and derivatives of native NMTase. Such variants may be, e.g., a naturally occurring allelic variant of native NMTase, a homolog of native NMTase, or a non-naturally occurring variant of native NMTase. These variants have a nucleotide sequence that differs from native NMTase in one or more bases. For example, the nucleotide sequence of such variants can feature a deletion, addition, or substitution of one or more nucleotides of a native NMTase. Nucleic acid insertions are preferably of about 1 to 10 contiguous nucleotides, and deletions are preferably of about 1 to 30 contiguous nucleotides.

In some applications, variant nucleic acid molecules encode polypeptides that substantially maintain an NMTase functional activity. For other applications, variant nucleic acid molecules encode polypeptides that lack or feature a significant reduction in an NMTase functional activity. Where it is desired to retain a functional activity of native NMTase, preferred variant nucleic acids feature silent or conservative nucleotide changes.

In other applications, variant NMTase polypeptides displaying substantial changes in one or more functional activities of native NMTase can be generated by making nucleotide substitutions that cause less than conservative changes in the encoded polypeptide. Examples of such nucleotide substitutions are those that cause changes in (a) the structure of the polypeptide backbone; (b) the charge or hydrophobicity of the polypeptide; or (c) the bulk of an amino acid side chain. Nucleotide substitutions generally expected to produce the greatest changes in protein properties are those that cause non-conservative changes in codons. Examples of codon changes that are likely to cause major changes in protein structure are those that cause substitution of (a) a hydrophilic residue, e.g., serine or threonine, for (or by) a hydrophobic residue, e.g., leucine, isoleucine, phenylalanine, valine or alanine; (b) a cysteine or proline for (or by) any other residue; (c) a residue having an electropositive side chain, e.g., lysine, arginine, or histadine, for (or by) an electronegative residue, e.g., glutamine or aspartine; or (d) a residue having a bulky side chain, e.g., phenylalanine, for (or by) one not having a side chain, e.g., glycine.

Naturally occurring allelic variants of native NMTase within the invention are nucleic acids isolated from *L. latifolium* that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native NMTase, and encode polypeptides having as at least one functional activity in common with native NMTase. Homologs of native NMTase within the invention are nucleic acids isolated from other species that have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native NMTase, and encode polypeptides having at least one functional activity in common with native NMTase. Naturally occurring allelic variants of NMTase and homologs of NMTase can be isolated by screening $L.$ $latifolium$ and non-$L.$ $latifolium$ (respectively) for a native NMTase functional activity (e.g., β-alanine methylation) using a library screen similarly to the method of identification of native NMTase described herein, other assays described herein, or other techniques known in the art. The nucleotide sequence of such homologs and allelic variants can be determined by conventional DNA sequencing methods. Alternatively, public or non-proprietary nucleic acid databases can be searched to identify other nucleic acid molecules having a high percent (e.g., 70, 80, 90% or more) sequence identity to native NMTase. Once identified, these sequences can be incorporated into expression constructs that can be used in various assays such as those described herein to screen for those molecules that encode proteins which share or lack one or more functional activities of native NMTase.

Non-naturally occurring NMTase variants are nucleic acids that do not occur in nature (e.g., are made by the hand of man), have at least 75% (e.g., 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%) sequence identity with native NMTase, and encode polypeptides having as at least one functional activity in common with native NMTase. Examples of non-naturally occurring NMTase nucleic acids are those that encode a fragment of an NMTase protein, those that hybridize to native NMTase or a complement of native NMTase under stringent conditions, those that share at least 65% sequence identity with native NMTase or a complement of native NMTase, and those that encode an NMTase fusion protein.

Nucleic acids encoding fragments of NMTase within the invention are those that encode, e.g., 2, 5, 10, 25, 50, 100, 150, 200, 250, 300, or more amino acid residues of NMTase. Shorter oligonucleotides (e.g., those of 6, 12, 20, 30, 50, 100, 125, 150 or 200 base pairs in length) that encode or hybridize with nucleic acids that encode fragments of NMTase can be used as probes, primers, or antisense molecules. Longer polynucleotides (e.g., those of 300, 400, 500, 600, 700, 800, 900, 1000, 1100, 1200 or 1300 base pairs) that encode or hybridize with nucleic acids that encode fragments of NMTase can be used in place of native NMTase in applications where it is desired to modulate a functional activity of native NMTase. Nucleic acids encoding fragments of NMTase can be made by enzymatic digestion (e.g., using a restriction enzyme) or chemical degradation of full length NMTase or variants of NMTase.

Nucleic acids that hybridize under stringent conditions to the nucleic acid of SEQ ID NO:28 or the complement of SEQ ID NO:28 are also within the invention. For example, such nucleic acids can be those that hybridize to SEQ ID NO:28 or the complement of SEQ ID NO:28 under low stringency conditions, moderate stringency conditions, or high stringency conditions are within the invention. Preferred such nucleotide acids are those having a nucleotide sequence that is the complement of all or a portion of SEQ ID NO:28. Other variants of NMTase within the invention are polynucleotides that share at least 65% (e.g., 65, 70, 75, 80, 85, 90, 91, 92, 93, 94, 95, 96, 97, 98, and 99%) sequence identity to SEQ ID NO:28 or the complement of SEQ ID NO:28. Nucleic acids that hybridize under stringent conditions to or share at least 65% sequence identity with SEQ ID NO:28 or the complement of SEQ ID NO:28 can be obtained by techniques known in the art such as by making mutations in native NMTase, by isolation from an organism expressing such a nucleic acid (e.g., a $L.$ $latifolium$ plant expressing a variant of native NMTase), or a non-$L.$ $latifolium$ plant expressing a homolog of native NMTase.

Nucleic acid molecules encoding NMTase fusion proteins are also within the invention. Such nucleic acids can be made by preparing a construct (e.g., an expression vector) that expresses an NMTase fusion protein when introduced into a suitable host. For example, such a construct can be made by ligating a first polynucleotide encoding an NMTase protein fused in frame with a second polynucleotide encoding another protein such that expression of the construct in a suitable expression system yields a fusion protein.

The oligonucleotides of the invention can be DNA or RNA or chimeric mixtures or derivatives or modified versions thereof, single-stranded or double-stranded. Such oligonucleotides can be modified at the base moiety, sugar moiety, or phosphate backbone, for example, to improve stability of the molecule, hybridization, etc. Oligonucleotides within the invention may additionally include other appended groups such as peptides (e.g., for targeting host cell receptors in vivo), or agents facilitating transport across the cell membrane (see, e.g., Letsinger et al. (1989) Proc. Natl. Acad. Sci. USA 86:6553–6556; Lemaitre et al. (1987) Proc. Natl. Acad. Sci. USA 84:648–652; PCT Publication No. WO 88/09810, published Dec. 15, 1988), hybridization-triggered cleavage agents. (See, e.g., Krol et al. (1988) BioTechniques 6:958–976) or intercalating agents. (See, e.g., Zon (1988) Pharm. Res. 5:539–549). To this end, the oligonucleotides may be conjugated to another molecule, e.g., a peptide, hybridization triggered cross-linking agent, transport agent, hybridization-triggered cleavage agent, etc.

Using the nucleotide sequence of native NMTase and the amino acid sequence of the NMTase polypeptides disclosed herein, those skilled in the art can create nucleic acid molecules that have minor variations in their nucleotides, by, for example, standard nucleic acid mutagenesis techniques or by chemical synthesis. Variant NMTase nucleic acid molecules can be expressed to produce variant NMTase polypeptides.

Antisense, Ribozyme, Triplex, and RNA Interference Techniques

Although a major application of the invention involves increasing a plant cell's or plant's stress tolerance by increasing the expression of NMTase in the plant cell or plant, in other applications it may be desired to decrease NMTase expression in a cell. Thus, another aspect of the invention relates to the use of purified antisense nucleic acids to inhibit expression of NMTase. Antisense nucleic acid molecules within the invention are those that specifically hybridize (e.g. bind) under cellular conditions to cellular mRNA and/or genomic DNA encoding an NMTase protein in a manner that inhibits expression of the NMTase protein, e.g., by inhibiting transcription and/or translation. The binding may be by conventional base pair complementarity, or, for example, in the case of binding to DNA duplexes, through specific interactions in the major groove of the double helix.

Antisense constructs can be delivered, for example, as an expression plasmid which, when transcribed in the cell, produces RNA which is complementary to at least a unique portion of the cellular mRNA which encodes an NMTase protein. Alternatively, the antisense construct can take the form of an oligonucleotide probe generated ex vivo which, when introduced into an NMTase expressing cell, causes inhibition of NMTase expression by hybridizing with an mRNA and/or genomic sequences coding for NMTase. Such oligonucleotide probes are preferably modified oligonucleotides that are resistant to endogenous nucleases, e.g. exonucleases and/or endonucleases, and are therefore stable in vivo. Exemplary nucleic acid molecules for use as antisense oligonucleotides are phosphoramidate, phosphothioate and methylphosphonate analogs of DNA (see, e.g., U.S. Pat. Nos. 5,176,996; 5,264,564; and 5,256,775). Additionally, general approaches to constructing oligomers useful in antisense therapy have been reviewed, for example, by Van der Krol et al. (1988) Biotechniques 6:958–976; and Stein et al. (1988) Cancer Res 48:2659–2668. With respect to antisense DNA, oligodeoxyribonucleotides derived from the translation initiation site, e.g., between the −10 and +10 regions of an NMTase encoding nucleotide sequence, are preferred.

Antisense approaches involve the design of oligonucleotides (either DNA or RNA) that are complementary to NMTase mRNA. The antisense oligonucleotides will bind to NMTase mRNA transcripts and prevent translation. Absolute complementarity, although preferred, is not required. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. Wagner, R. Nature 372:333, 1994. Therefore, oligonucleotides complementary to either the 5' or 3' untranslated, non-coding regions of an NMTase gene could be used in an antisense approach to inhibit translation of endogenous NMTase mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5', 3' or coding region of NMTase mRNA, antisense nucleic acids should be at least six nucleotides in length, and are preferably less that about 100 and more preferably less than about 50, 25, 17 or 10 nucleotides in length.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein.

Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209, 1988), and methylphosphonate oligonucleotides can be prepared by use of controlled pore glass polymer supports (Sarin et al., Proc. Natl. Acad. Sci. USA 85:7448–7451, 1988), etc.

The antisense molecules should be delivered into cells that express NMTase in vivo. A number of methods have been developed for delivering antisense DNA or RNA into cells. For instance, antisense molecules can be introduced directly into the tissue site using bombardment-based methodology (see, e. g., Christou P, Plant Mol Biol 35:197, 1997) or by Agrobacterium-mediated transformation (see, e.g., Hiei et al., Plant Mol Biol 35:205, 1997). Alternatively, modified antisense molecules, designed to target the desired cells (e.g., antisense linked to peptides or antibodies that specifically bind receptors or antigens expressed on the target cell surface) can be used.

Because it is often difficult to achieve intracellular concentrations of the antisense sufficient to suppress translation on endogenous mRNAs, a preferred approach utilizes a recombinant DNA construct in which the antisense oligonucleotide is placed under the control of a strong promoter. The use of such a construct to transform *L. latifolium* plants will result in the transcription of sufficient amounts of single stranded RNAs that will form complementary base pairs with the endogenous NMTase transcripts and thereby prevent translation of NMTase mRNA.

In addition to antisense-based methods, NMTase activity can also be inhibited in a cell using other technologies including ribozymes, gene inactivation, and RNA interference. Ribozyme molecules designed to catalytically cleave NMTase mRNA transcripts can also be used to prevent translation of NMTase mRNA and expression of NMTase. See, e.g., PCT Publication No. WO 90/11364, published Oct. 4, 1990; Sarver et al., Science 247:1222–1225, 1990; U.S. Pat. No. 5,093,246; and Haseloff and Gerlach, Nature 334:585–591, 1988. Endogenous NMTase gene expression can also be reduced by inactivating or "knocking out" the NMTase gene or its promoter using targeted homologous recombination. See, e.g., Kempin et al., Nature 389:802, 1997; Smithies et al., Nature 317:230–234, 1985; Thomas and Capecchi, Cell 51:503–512, 1987; and Thompson et al., Cell 5:313–321, 1989. Alternatively, endogenous NMTase gene expression might be reduced by targeting deoxyribonucleotide sequences complementary to the regulatory region of the NMTase gene (i.e., the NMTase promoter and/or enhancers) to form triple helical structures that prevent transcription of the NMTase gene in target cells. (See generally, Helene, C. Anticancer Drug Des. 6(6):569–84, 1991; Helene, C., et al., Ann. N. Y. Acad. Sci. 660:27–36, 1992; and Maher, L. J., Bioassays 14(12):807–15, 1992).

Another technique that may be employed to modulate NMTase expression is RNA interference (RNAi). Chuang and Meyerowicz, Proc. Nat=l Acad. Sci. USA, 97:4985, 2000. In this technique, double-stranded RNA (dsRNA)-expressing constructs are introduced into a plant using, e.g., Agrobacterium-mediated transformation. In this manner, such dsRNA is persistent and inherited. By selecting appropriate sequences (e.g., those corresponding to NMTase), expression of dsRNA can interfere with accumulation of endogenous mRNA encoding a target protein (e.g., NMTase).

Probes and Primers

The invention also includes oligonucleotide probes (i.e., isolated nucleic acid molecules conjugated with a detectable label or reporter molecule, e.g., a radioactive isotope, ligand, chemiluminescent agent, or enzyme); and oligonucleotide primers (i.e., isolated nucleic acid molecules that can be annealed to a complementary target DNA strand by nucleic acid hybridization to form a hybrid between the primer and the target DNA strand, then extended along the target DNA strand by a polymerase, e.g., a DNA polymerase). Primer pairs can be used for amplification of a nucleic acid sequence, e.g., by the polymerase chain reaction (PCR) or other conventional nucleic-acid amplification methods. Probes and primers within the invention are generally 15 nucleotides or more in length, preferably 20 nucleotides or more, more preferably 25 nucleotides, and most preferably 30 nucleotides or more. Preferred probes and primers are those that hybridize to the native NMTase sequence (SEQ ID NO: 28) under high stringency conditions, and those that hybridize to NMTase homologs under at least moderately stringent conditions. Preferably, probes and primers according to the present invention have complete sequence identity with the native L. latifolium NMTase sequence, although probes differing from the L. latifolium NMTase sequence and that retain the ability to hybridize to native NMTase sequences under stringent conditions may be designed by conventional methods. Primers and probes based on the native L. latifolium NMTase sequences disclosed herein can be used to confirm (and, if necessary, to correct) the disclosed NMTase sequences by conventional methods, e.g., by re-cloning and sequencing a L. latifolium NMTase cDNA.

Vectors for Expressing NMTase

Natural or synthetic nucleic acids according to the present invention can be incorporated into recombinant nucleic acid constructs, typically DNA constructs, capable of introduction into and replication in a host cell. Such a construct preferably is a vector that includes a replication system and sequences that are capable of transcription and translation of a polypeptide-encoding sequence in a given host cell. For the practice of the present invention, conventional compositions and methods for preparing and using vectors and host cells are employed, as discussed, e.g., in Sambrook et al., supra, or Ausubel et al., supra.

Expression (or increased expression) of NMTase genes in plants is achieved by introducing into a plant a nucleic acid sequence containing an NMTase gene encoding an NMTase polypeptide. A number of vectors suitable for stable transformation of plant cells or for the establishment of transgenic plants are known. See, e.g., Pouwels et al. (1985) Cloning Vectors: A Laboratory Manual, Supp. 1987; Weissbach and Weissbach, (1989) Methods for Plant Molecular Biology, Academic Press; and Gelvin et al. (1990) Plant Molecular Biology Manual, Kluwer Academic Publishers. Typically, plant expression vectors include (1) one or more cloned plant genes under the transcriptional control of 5' and 3' regulatory sequences and (2) a dominant selectable marker. Such plant expression vectors may also contain, if desired, a promoter regulatory region (e.g., a regulatory region controlling inducible or constitutive, environmentally- or developmentally-regulated, or cell- or tissue-specific expression), a transcription initiation start site, a ribosome binding site, an RNA processing signal, a transcription termination site, and/or a polyadenylation signal.

An example of a useful plant promoter which could be used to express a plant resistance gene according to the invention is a cauliovirus promoter, e.g., the cauliflower mosaic virus (CaMV) 35S promoter. These promoters confer high levels of expression in most plant tissues, and are generally not dependent on the particular encoded proteins to be expressed. CaMV is a source for both the 35S and 19S promoters. In most tissues of transgenic plants, the CaMV 35S promoter is a strong promoter. See, e.g., Odel et al., Nature 313:810, 1985; Dekeyser et al., Plant Cell 2:591, 1990; Terada and Shimamoto, Mol. Gen. Genet. 220:389, 1990. Other plant promoters that may be useful in the invention are known. See, e.g., An et al., Plant Physiol. 88:547, 1988; Fromm et al., Plant Cell 1:977, 1989; Callis et al. Plant Physiol. 88: 965, 1988; Kuhlemeier et al., Plant Cell 1: 471, 1989; Schaffner and Sheen, Plant Cell 3: 997, 1991; Simpson et al., EMBO J. 4: 2723, 1985; Marcotte et al., Plant Cell 1:969, 1989; Siebertz et al., Plant Cell 1: 961, 1989; Roshal et al., EMBO J. 6:1155, 1987; Schemthaner et al., EMBO J. 7: 1249, 1988; and Bustos et al., Plant Cell 1:839, 1989.

Plant expression vectors may also include RNA processing signals such as introns, which have been shown to be important for efficient RNA synthesis and accumulation. Callis et al., Genes and Dev. 1: 1183, 1987. The location of the RNA splice sequences can influence the level of transgene expression in plants. In view of this fact, an intron may be positioned upstream or downstream of an NMTase polypeptide-encoding sequence in the transgene to modulate levels of gene expression.

Expression vectors within the invention may also include regulatory control regions which are generally present in the 3' regions of plant genes. See, e.g., Thornburg et al., Proc. Natl Acad. Sci USA 84: 744, 1987; An et al., Plant Cell 1: 115, 1989. For example, a 3' terminator region may be included in the expression vector to increase stability of the mRNA. For instance, 3' terminators derived from octopine or nopaline synthase genes could be used.

Plant expression vector within the invention preferably contain a selectable marker gene used to identify the cells that have become transformed. Suitable selectable marker genes for plant systems include genes encoding enzymes that produce antibiotic resistance (e.g., those conferring resistance to hygromycin, kanamycin, bleomycin, G418, streptomycin or spectinomycin) or herbicide resistance (e.g., phosphinothricin acetyltransferase which confers resistance to the herbicide Basta (Hoechst AG, Frankfurt, Germany). A useful strategy for selection of transformants for herbicide resistance is described in Vasil I K (1984) Cell Culture and Somatic Cell Genetics of Plants, Vol I, II, III Laboratory Procedures and Their Applications Academic Press, New York.

Cells Transformed with NMTase

Upon construction of the plant expression vector, several standard methods are known for introducing recombinant genetic material into a host plant to make a transgenic plant. Examples of such methods include (1) Agrobacterium-mediated transformation (*A. tumefaciens* or *A. rhizogenes*) (see, e.g., Lichtenstein and Fuller In: Genetic Engineering, vol 6, P W J Rigby, ed, London, Academic Press, 1987; and Lichtenstein, C. P., and Draper, J,. In: DNA Cloning, Vol II, D. M. Glover, ed, Oxford, IRI Press, 1985), (2) the particle delivery system (see, e.g., Gordon-Kamm et al., Plant Cell 2:603, (1990); or BioRad Technical Bulletin 1687, supra), (3) microinjection protocols (see, e.g., Green et al., Plant Tissue and Cell Culture, Academic Press, New York, 1987), (4) polyethylene glycol (PEG) procedures (see, e.g., Draper et al., Plant Cell Physiol 23:451, (1982); or e.g., Zhang and Wu, Theor. Appl. Genet. 76:835, (1988)), (5) liposome-mediated DNA uptake (see, e.g., Freeman et al., Plant Cell Physiol 25: 1353, (1984)), (6) electroporation protocols (see, e.g., Gelvin et al supra; Dekeyser et al. supra; or Fromm et al Nature 319: 791, (1986)), and (7) the vortexing method (see, e.g., Kindle, K., Proc. Natl. Acad. Sci., USA 87:1228, (1990)). *Agrobacterium*-mediated plant transformation is typically carried out in two phases. First, all the cloning and DNA modification steps are done in *E. coli*, and the plasmid containing the gene construct of interest is transferred by conjugation into *Agrobacterium*. Second, the resulting *Agrobacterium* strain is used to transform plant cells. Thus, for the generalized plant expression vector, the plasmid contains an origin of replication that allows it to replicate in *Agrobacterium* and a high copy number origin of replication functional in *E. coli*. This permits facile production and testing of transgenes in *E. coli* prior to transfer to *Agrobacterium* for subsequent introduction into plants. Resistance genes can be carried on the vector, one for selection in bacteria, e.g., streptomycin, and the other that will express in plants, e.g., a gene encoding for kanamycin resistance or an herbicide resistance gene. Also present are restriction endonuclease sites for the addition of one or more transgenes operably linked to appropriate regulatory sequences and directional T-DNA border sequences which, when recognized by the transfer functions of *Agrobacterium*, delimit the region that will be transferred to the plant.

In another example, plant cells may be transformed by shooting into the cell tungsten microprojectiles on which cloned DNA is precipitated. In the Biolistic Apparatus (Bio-Rad, Hercules, Calif.) used for the shooting, a gunpowder charge (0.22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to go through. As a result, the plastic macroprojectile smashes against the stopping plate and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

Transgenic Plants

Transgenic plants within the invention can be made by regenerating plant cells transformed with a plant expression vector by standard plant tissue culture techniques. See, e.g., in Vasil supra; Green et al., supra; Weissbach and Weissbach, supra; and Gelvin et al., supra. For example, a vector carrying a selectable marker gene (e.g., kanamycin resistance), a cloned NMTase gene under the control of its own promoter and terminator or, if desired, under the control of exogenous regulatory sequences such as the 35S CaMV promoter and the nopaline synthase terminator is transformed into *Agrobacterium*. Transformation of leaf tissue with vector-containing *Agrobacterium* is carried out as described in Ishida et al., Nature Biotech. 14:745–750, 1996 and Horsch et al., Science 227:1229, 1985. Putative transformants are selected after a few weeks (e.g., 3 to 5 weeks) on plant tissue culture media containing kanamycin (e.g. 100 µg/ml). Kanamycin-resistant shoots are then placed on plant tissue culture media without hormones for root initiation. Kanamycin-resistant plants are then selected for greenhouse growth. If desired, seeds from self-fertilized transgenic plants can then be sowed in a soil-less media and grown in a greenhouse. Kanamycin-resistant progeny are selected by sowing surfaced sterilized seeds on hormone-free kanamycin-containing media. Analysis for the integration of the transgene is accomplished by standard techniques (see, e.g., Ausubel et al. supra; Gelvin et al. supra). Transgenic plants expressing the selectable marker are then screened for transmission of the transgene DNA by standard immunoblot and DNA and RNA detection techniques. Each positive transgenic plant and its transgenic progeny are unique in comparison to other transgenic plants established with the same transgene. Integration of the transgene DNA into the plant genomic DNA is in most cases random and the site of integration can profoundly effect the levels, and the tissue and developmental patterns of transgene expression. Consequently, a number of transgenic lines are usually screened for each transgene to identify and select plants with the most appropriate expression profiles.

Transgenic lines are evaluated for levels of transgene expression. Expression at the RNA level is determined initially to identify and quantitate expression-positive plants. Standard techniques for RNA analysis are employed and include PCR amplification assays using oligonucleotide primers designed to amplify only transgene RNA templates and solution hybridization assays using transgene-specific probes (see, e.g., Ausubel et al., supra). The RNA-positive plants are then analyzed for protein expression by Western immunoblot analysis using NMTase polypeptide-specific antibodies (see below and Ausubel et al., supra). In addition, in situ hybridization and immunocytochemistry according to standard protocols can be done using transgene-specific nucleotide probes and antibodies, respectively, to localize sites of expression within transgenic tissue.

Purified β-alanine NMTase Polypeptides

The present invention provides a purified β-alanine NMTase polypeptide isolated from *L. latifolium*. As described in the Examples section below, a β-alanine NMTase was isolated from *L. latifolium* using a series of purification steps. This protein was characterized both physically and functionally. Isoelectric focusing analysis showed that the purified enzyme exhibited an isoelectric point of 5.15. SDS-PAGE analysis showed that the purified enzyme migrated at about 43 kD. Functionally, the purified enzyme was capable of methylating β-alanine, N-methyl β-alanine, and N,N-dimethyl β-alanine.

In addition to the whole β-alanine NMTase polypeptide, the invention also provides fragments of the enzyme. Fragments of the enzyme can be made by treating the whole β-alanine NMTase polypeptide with one or more proteases, or by subjecting it to one of the techniques described below in the examples section. Peptide sequencing revealed the amino acid sequence of 5 oligopeptides (SEQ ID NOs: 1–5, 9, 10, and 11) making up parts of the whole β-alanine NMTase polypeptide. Thus, the invention also provides purified polypeptides including one or more of these sequences. Fragments of the whole β-alanine NMTase polypeptide can be made by chemically synthesizing the oligopeptides by known techniques.

In another aspect, the present invention provides a purified NMTase polypeptide encoded by a nucleic acid of the invention. A preferred form of NMTase is a purified native NMTase polypeptide that has the deduced amino acid sequence shown in FIG. 7B (SEQ ID NO. 29) or which is encoded by the nucleic acid of SEQ ID NO:28 (FIG. 7A). Variants of native NMTase such as fragments, analogs and derivatives of native NMTase are also within the invention. Such variants include, e.g., a polypeptide encoded by a naturally occurring allelic variant of native NMTase, a polypeptide encoded by a homolog of native NMTase, and a polypeptide encoded by a non-naturally occurring variant of native NMTase.

NMTase variants have a peptide sequence that differs from native NMTase in one or more amino acids. The peptide sequence of such variants can feature a deletion, addition, or substitution of one or more amino acids of a native NMTase polypeptide. Amino acid insertions are preferably of about 1 to 4 contiguous amino acids, and deletions are preferably of about 1 to 10 contiguous amino acids. In some applications, variant NMTase polypeptides substantially maintain a native NMTase functional activity. For other applications, variant NMTase polypeptides lack or feature a significant reduction in an NMTase functional activity. Where it is desired to retain a functional activity of native NMTase, preferred NMTase variants can be made by expressing nucleic acid molecules within the invention that feature silent or conservative changes. Variant NMTase polypeptides with substantial changes in functional activity can be made by expressing nucleic acid molecules within the invention that feature less than conservative changes.

NMTase fragments corresponding to one or more particular motifs and/or domains or to arbitrary sizes, for example, at least 5, 10, 25, 50, 75, 100, 125, 150, 175, 200, 250, 300, and 350 amino acids in length are within the scope of the present invention. Isolated peptidyl portions of NMTase proteins can be obtained by screening peptides recombinantly produced from the corresponding fragment of the nucleic acid encoding such peptides. In addition, fragments can be chemically synthesized using techniques known in the art such as conventional Merrifield solid phase f-Moc or t-Boc chemistry. For example, an NMTase polypeptide of the present invention may be arbitrarily divided into fragments of desired length with no overlap of the fragments, or preferably divided into overlapping fragments of a desired length. The fragments can be produced (recombinantly or by chemical synthesis) and tested to identify those peptidyl fragments which can function as either agonists or antagonists of native NMTase.

Another aspect of the present invention concerns recombinant forms of the NMTase proteins. Recombinant polypeptides preferred by the present invention, in addition to native NMTase, are encoded by a nucleic acid that has at least 85% sequence identity (e.g., 85, 86, 87, 88, 89, 90, 91, 92, 93, 94, 95, 96, 97, 98, 99, 100%) with the nucleic acid sequence of SEQ ID NO:28. In a preferred embodiment, an NMTase protein of the present invention is a Plumbaginaceae NMTase protein. In particularly preferred embodiment, an NMTase protein has one or more functional activities of native NMTase.

NMTase variants can be generated through various techniques known in the art. For example, NMTase variants can be made by mutagenesis, such as by introducing discrete point mutation(s), or by truncation. Mutation can give rise to an NMTase variant having substantially the same, or merely a subset of the biological activity of native NMTase. Other variants of NMTase that can be generated include those that are resistant to proteolytic cleavage, as for example, due to mutations which alter ubiquitination or other enzymatic targeting associated with the protein. Whether a change in the amino acid sequence of a peptide results in an NMTase variant having one or more functional activities of native NMTase can be readily determined by testing the variant for a native NMTase functional activity in one or more of the assays described herein.

As another example, NMTase variants can be generated from a degenerate oligonucleotide sequence. Chemical synthesis of a degenerate gene sequence can be carried out in an automatic DNA synthesizer, and the synthetic genes then ligated into an appropriate expression vector. The purpose of a degenerate set of genes is to provide, in one mixture, all of the sequences encoding the desired set of potential NMTase sequences. The synthesis of degenerate oligonucleotides is well known in the art. See e.g., Narang, S A (1983) Tetrahedron 39:3; Itakura et al. (1981) Recombinant DNA, Proc 3rd Cleveland Sympos. Macromolecules, ed. A G Walton, Amsterdam: Elsevier pp 273–289; Itakura et al., Annu. Rev. Biochem. 53:323, 1984; Itakura et al., Science 198:1056, 1984; Ike et al., Nucleic Acid Res. 11:477, 1983. Such techniques have been employed in the directed evolution of other proteins. See e.g., Scott et al. Science 249:386–390, 1990; Roberts et al., Proc. Natl. Acad. Sci. USA 89:2429–2433, 1992; Devlin et al., Science 249: 404–406, 1990; Cwirla et al., Proc. Natl. Acad. Sci. USA 87: 6378–6382, 1990; as well as U.S. Pat. Nos. 5,223,409, 5.198,346, and 5,096,815.

Similarly, a library of coding sequence fragments can be provided for an NMTase clone in order to generate a variegated population of NMTase fragments for screening and subsequent selection of fragments having one or more native NMTase functional activities. A variety of techniques are known in the art for generating such libraries, including chemical synthesis. In one embodiment, a library of coding sequence fragments can be generated by (i) treating a double stranded PCR fragment of an NMTase coding sequence with a nuclease under conditions wherein nicking occurs only about once per molecule; (ii) denaturing the double stranded DNA; (iii) renaturing the DNA to form double stranded DNA which car include sense/antisense pairs from different nicked products; (iv) removing single stranded portions from reformed duplexes by treatment with S1 nuclease; and (v) ligating the resulting fragment library into an expression vector. By this exemplary method, an expression library can be derived which codes for N-terminal, C-terminal and internal fragments of various sizes.

A wide range of techniques are known in the art for screening gene products of combinatorial libraries made by point mutations or truncation, and for screening cDNA libraries for gene products having a certain property. Such techniques will be generally adaptable for rapid screening of the gene libraries generated by the combinatorial mutagenesis of NMTase variants. The most widely used techniques for screening large gene libraries typically comprise cloning the gene library into replicable expression vectors, transforming appropriate cells with the resulting library of vectors, and expressing the combinatorial genes under conditions in which detection of a desired activity facilitates relatively easy isolation of the vector encoding the gene whose product was detected. Each of the illustrative assays described below are amenable to high through-put analysis as necessary to screen large numbers of degenerate NMTase sequences created by combinatorial mutagenesis techniques.

Combinatorial mutagenesis has a potential to generate very large libraries of mutant proteins, e.g., in the order of $10^{26}$ molecules. Combinatorial libraries of this size may be technically challenging to screen even with high throughput screening assays. To overcome this problem, techniques such as recursive ensemble mutagenesis (REM) that allow one to avoid the very high proportion of non-functional proteins in a random library and simply enhance the frequency of functional proteins (thus decreasing the complexity required to achieve a useful sampling of sequence space) can be used. REM is an algorithm which enhances the frequency of functional mutants in a library when an appropriate selection or screening method is employed. Arkin and Yourvan (1992) Proc. Natl. Acad. Sci. USA 89:7811–7815; Yourvan et al. (1992) Parallel Problem Solving from Nature, 2., In Maenner and Manderick, eds., Elsevier Publishing Co., Amsterdam, pp. 401–410; Delgrave et al. (1993) Protein Engineering 6(3):327–331. A technique such as RACHITT (random chimeragenesis on transient templates) can also be used to generate a combinatorial library of mutant proteins. RACHITT is a method of in vitro recombination or "DNA shuffling" that yields a high recombinatorial frequency, a large spectrum of phenotypic diversity, and a low frequency of nonfunctional clones. Coco et al., Nature Biotech. 19:354–358, 2001.

The invention also provides for reduction of NMTase proteins to generate mimetics. Thus, the mutagenic techniques described can also be used to map which determinants of NMTase participate in protein-protein interactions involved in, for example, binding of NMTase to proteins which may function upstream (including both activators and repressors of its activity) of NMTase or to proteins or nucleic acids which may function downstream of NMTase, and whether such molecules are positively or negatively regulated by NMTase. To illustrate, the critical residues of NMTase which are involved in molecular recognition of, for example, NMTase or other components upstream or downstream of NMTase can be determined and used to generate NMTase-derived peptidomimetics which competitively inhibit binding of NMTase with that moiety. By employing, for example, scanning mutagenesis to map the amino acid residues of NMTase that are involved in catalyzing methylation reactions, peptidomimetic compounds can be generated which mimic those residues of native NMTase. Such mimetics may then be used to interfere with the normal function of an NMTase protein. For instance, non-hydrolyzable peptide analogs of such residues can be generated using benzodiazepine (e.g., see Freidinger et al. (1988) in Peptides: Chemistry and Biology, G. R. Marshall ed., ESCOM Publisher: Leiden, Netherlands), azepine (e.g., see Huffinan et al. (1988) in Peptides: Chemistry and Biology, G. R. Marshall ed., ESCOM Publisher: Leiden, Netherlands), substituted gamma lactam rings (Garvey et al. (1988) in Peptides: Chemistry and Biology, G. R. Marshall ed., ESCOM Publisher: Leiden, Netherlands), keto-methylene pseudo peptides (Ewenson et al., J. Med. Chem. 29:295, 1986; and Ewenson et al. (1985) in Peptides: Structure and Function (Proceedings of the 9th American Peptide Symposium) Pierce Chemical Co. Rockland, Ill.), beta-turn dipeptide cores (Nagai et al., Tetrahedron Lett 26:647, 1985; and Sato et al., J. Chem. Soc. Perkin. Trans. 1:1231, 1986), and b-aminoalcohols (Gordon et al., Biochem. Biophys. Res. Commun. 126:419, 1985; and Dann et al., Biochem. Biophys. Res. Commun. 134:71, 1986). NMTase polypeptides may also be chemically modified to create NMTase derivatives by forming covalent or aggregate conjugates with other chemical moieties, such as glycosyl groups, lipids, phosphate, acetyl groups and the like. Covalent derivatives of NMTase can be prepared by linking the chemical moieties to functional groups on amino acid sidechains of the protein or at the N-terminus or at the C-terminus of the polypeptide.

The present invention further pertains to methods of producing the subject NMTase polypeptides. For example, a host cell transfected with a nucleic acid vector directing expression of a nucleotide sequence encoding the subject polypeptides can be cultured under appropriate conditions to allow expression of the peptide to occur. The cells may be harvested, lysed, and the protein isolated. A recombinant NMTase polypeptide can be isolated from host cells using techniques known in the art for purifying proteins including ion-exchange chromatography, gel filtration chromatography, ultrafiltration, electrophoresis, and immunoaffinity purification with antibodies specific for such peptide.

For example, after NMTase has been expressed in any cell or in a transgenic plant (e.g., as described above), it can be isolated using any immuno-affinity chromatography. For instance, an anti-NMTase antibody (e.g., produced as described below) can be immobilized on a column chromatography matrix, and the matrix can be used for immuno-affinity chromatography to purify NMTase from cell lysates by standard methods. See e.g., Ausubel et al., supra. After immuno-affinity chromatography, NMTase can be further purified by other standard techniques, e.g., high performance liquid chromatography. See e.g., Fisher (1980) Laboratory Techniques In Biochemistry And Molecular Biology, Work and Burdon, eds., Elsevier. In another embodiment, NMTase is expressed as a fusion protein containing an affinity tag (e.g., GST) that facilitates its purification.

Anti-βalanine NMTase Antibodies

β-alanine NMTase polypeptides (or immunogenic fragments or analogs thereof) can be used to raise antibodies useful in the invention. Such polypeptides can be isolated as described herein. Fragments of β-alanine NMTase can be prepared by digesting the native protein with proteases or by synthesizing oligopeptides based on known amino acid sequence information. In general, β-alanine NMTase polypeptides can be coupled to a carrier protein, such as KLH, as described in Ausubel et al., supra, mixed with an adjuvant, and injected into a host mammal. Antibodies produced in that animal can then be purified by peptide antigen affinity chromatography. In particular, various host animals can be immunized by injection with a β-alanine NMTase polypeptide or an antigenic fragment thereof. Commonly employed host animals include rabbits, mice, guinea pigs, and rats. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Other potentially useful adjuvants include BCG (bacille Calmette-Guerin) and *Corynebacterium parvum*.

Polyclonal antibodies are heterogeneous populations of antibody molecules that are contained in the sera of the immunized animals. Antibodies within the invention therefore include polyclonal antibodies and, in addition, monoclonal antibodies, single chain antibodies, Fab fragments, $F(ab')_2$ fragments, and molecules produced using a Fab expression library. Monoclonal antibodies, which are homogeneous populations of antibodies to a particular antigen, can be prepared using the β-alanine NMTase polypeptides described above and standard hybridoma technology. See e.g., Kohler et al., Nature 256:495, 1975; Kohler et al., Eur. J. Immunol. 6:511, 1976; Kohler et al., Eur. J. Immunol. 6:292, 1976; Hammerling et al. (1981) Monoclonal Antibodies and T Cell Hybridomas, Elsevier, N.Y.; Ausubel et al., supra. In particular, monoclonal antibodies can be obtained by any technique that provides for the production of antibody molecules by continuous cell lines in culture such as described in Kohler et al., Nature 256:495, 1975; and U.S. Pat. No. 4,376,110; the human B-cell hybridoma technique (Kosbor et al., Immunology Today 4:72, 1983; Cole et al., Proc. Natl. Acad. Sci. USA 80:2026, 1983), and the EBV-hybridoma technique (Cole et al., 1983Monoclonal Antibodies and Cancer Therapy, Alan R. Liss, Inc., pp. 77–96). Such antibodies can be of any immunoglobulin class including IgG, IgM, IgE, IgA, IgD and any subclass thereof. A hybridoma producing a mAb of the invention may be cultivated in vitro or in vivo. The ability to produce high titers of mAbs in vivo makes this a particularly useful method of production.

Once produced, polyclonal or monoclonal antibodies can be tested for specific β-alanine NMTase recognition by Western blot or immunoprecipitation analysis by standard methods, for example, as described in Ausubel et al., supra. Antibodies that specifically recognize and bind to β-alanine NMTase are useful in the invention. For example, such antibodies can be used in an immunoassay to monitor the level of β-alanine NMTase produced by a plant (e.g., to determine the amount or subcellular location of β-alanine NMTase).

In some cases it may be desirable to minimize the potential problems of low affinity or specificity of antisera. In such circumstances, two or three fusions can be generated for each protein, and each fusion can be injected into at least two rabbits. Antisera can be raised by injections in a series, preferably including at least three booster injections. Antiserum is also checked for its ability to immunoprecipitate recombinant β-alanine NMTase polypeptides or control proteins, such as glucocorticoid receptor, CAT, or luciferase.

The antibodies of the invention can be used, for example, in the detection of β-alanine NMTase in a biological sample. Antibodies also can be used in a screening assay to measure the effect of a candidate compound on expression or localization of β-alanine NMTase. Additionally, such antibodies can be used to interfere with the interaction of β-alanine NMTase and other molecules that interact with β-alanine NMTase.

Techniques described for the production of single chain antibodies (U.S. Pat. Nos. 4,946,778, 4,946,778, and 4,704, 692) can be adapted to produce single chain antibodies against a β-alanine NMTase polypeptide, or a fragment thereof. Single chain antibodies are formed by linking the heavy and light chain fragments of the Fv region via an amino acid bridge, resulting in a single chain polypeptide.

Antibody fragments that recognize and bind to specific epitopes can be generated by known techniques. For example, such fragments include but are not limited to $F(ab')_2$ fragments that can be produced by pepsin digestion of the antibody molecule, and Fab fragments that can be generated by reducing the disulfide bridges of $F(ab')_2$ fragments. Alternatively, Fab expression libraries can be constructed (Huse et al., Science 246:1275, 1989) to allow rapid and easy identification of monoclonal Fab fragments with the desired specificity.

Detection of NMTase or Nucleic Acid Molecules Encoding NMTase

The invention encompasses methods for detecting the presence of NMTase protein or NMTase nucleic acid in a biological sample as well as methods for measuring the level of NMTase protein or NMTase nucleic acid in a biological sample. Such methods are useful for examining plant intracellular signaling pathways associated with stress resistance.

An exemplary method for detecting the presence or absence of NMTase in a biological sample involves obtaining a biological sample from a test plant (or plant cell) and contacting the biological sample with a compound or an agent capable of detecting an NMTase polypeptide or a nucleic acid encoding an NMTase polypeptide (e.g., mRNA or genomic DNA). A preferred agent for detecting a nucleic acid encoding an NMTase polypeptide is a labeled nucleic acid probe capable of hybridizing to the nucleic acid encoding the NMTase polypeptide. The nucleic acid probe can be, for example, all or a portion of NMTase itself (e.g., a nucleic acid molecule having the sequence of SEQ ID NO:28) or all or a portion of a complement of NMTase. Similarly, the probe can also be all or a portion of an NMTase variant, or all or a portion of a complement of an NMTase variant. For instance, oligonucleotides at least 15, 30, 50, 100, 250, or 500 nucleotides in length that specifically hybridize under stringent conditions to native NMTase or a complement of native NMTase can be used as probes within the invention.

A preferred agent for detecting an NMTase polypeptide is an antibody capable of binding to an NMTase polypeptide, preferably an antibody with a detectable label. Such antibodies can be polyclonal, or more preferably, monoclonal. An intact antibody, or a fragment thereof (e.g., Fab or $F(ab')_2$) can be used.

Detection methods of the invention can be used to detect an mRNA encoding NMTase, a genomic DNA encoding NMTase, or an NMTase polypeptide in a biological sample in vitro as well as in vivo. For example, in vitro techniques for detection of mRNAs encoding NMTase include Northern hybridizations and in situ hybridizations. In vitro techniques for detection of a NMTase polypeptide include enzyme linked immunosorbent assays (ELISAs), Western blots, immunoprecipitations and immunofluorescence. In vitro techniques for detection of genomic DNA encoding NMTase include Southern hybridizations. Furthermore, in vivo techniques for detection of a NMTase polypeptide include introducing into a plant or plant cell labeled anti-NMTase antibody. For example, the antibody can be labeled with a radioactive marker whose presence and location in a plant can be detected by standard imaging techniques.

EXAMPLES

The present invention is further illustrated by the following specific examples. The examples are provided for illustration only and are not to be construed as limiting the scope or content of the invention in any way.

Example 1

Materials and Methods

Chemicals. If not otherwise indicated, chemicals used were from Sigma Chemical Co (St. Louis, Mo.) and were of the highest purity available. Amberlite XAD-4 resin beads (Aldrich, Milwaukee, Wis.) were washed in 20 column volumes each of methanol and water and stored in water at 4° C. until use. S-Adenosyl-L-[methyl-$^3$H]Met was purchased from NEN Life Science Products (Boston, Mass.) at a specific activity of 82 Ci mmol$^{-1}$ (3 TBq mmol$^{-1}$) and used without further purification. S-Adenosyl-L-Met, chloride salt was purified using Whatman CM 52 ion exchange chromatography according to Chirpich (1968) Lysine-2,3-aminomutase: purification and properties. Ph.D. thesis. University of California, Berkeley. N-methyl β-alanine and N,N-dimethyl β-alanine were synthesized as described previously (Rathinasabapathi et al., Ann Bot 86:709–716, 2000). N,N-dimethyl β-alanine sepharose 4B affinity resin was prepared by coupling the amino group of 1,6 diaminohexane in EAH-sepharose (Amersham-Pharmacia Biotech, Piscataway, N.J.) to the carboxyl group of N,N-dimethyl β-alanine, using a carbodiimide procedure. Hoare and Datta (1990) Arch Biochem Biophys 277:122–129. Adenosine agarose affinity resin was prepared from 5'-AMP-agarose by the method of James et al. (1995) J. Biol. Chem. 270: 22344–22350. Magna Lift nylon (0.45μ, 137 mm) circles were from Osmonics, Inc. (Minnetonka, Minn.) dGTP (α-$^{32}$P, 800 Ci.mmol$^{-1}$) was purchased from Amersham Biosciences (Piscataway, N.J.). Plasmid purification and gel extraction kits were from Qiagen (Valencia, Calif.). RACE protocol kit was from BD Biosciences Clontech (Palo Alto, Calif.). Molecular weight markers, Taq polymerase, dNTPs and restriction enzymes were from Promega (Madison, Wis.). Oligonucleotide primers were synthesized from the custom primer synthesis unit of Life Technologies (Carlsbad, Calif.).

Plant Material. Seeds of *L. latifolium* (Sm.) O. Kuntze, were from Park Seed Co (Greenwood, S.C.). Plants were grown in Metro-Mix 200 (Scotts-Sierra, Marysville, Ohio) in wooden boxes (2 ft×2 ft×8 inches deep) in a greenhouse in Gainesville, Fla. The plants were fertilized once a week using a 200 ppm solution of a fertilizer (N:P:K 20:20:20). Other species of *Limonium* might also be used in the invention as a source of the NMTase. For acquiring RNA, *L. latifolium* and *L. sinuatum* plants were grown under controlled conditions in a greenhouse as described previously (Rathinasabapathi et al., Plant Physiol. 126:1241–1249, 2001). For salinity treatment, plants were grown in vermiculite and irrigated daily with half-strength Hoagland medium (Hoagland and Amon, 1950). Sodium chloride was added to the nutrient solution at 50 mM per every three days until reaching 200 mM. The plants were kept in this salinity for another week. Fully expanded leaves were harvested for RNA extraction.

Enzyme Extraction. Fully expanded leaves were harvested, briefly washed in a mild soap solution and rinsed in de-ionized water prior to extraction. Leaves were sliced into about 1 cm wide strips, frozen in liquid nitrogen and ground to a powder in a mortar. The powder was transferred to a blender containing freshly prepared extraction medium, 400 mL per 100 g fresh weight leaves. The extraction medium contained the following in 0.1 M Tris-HCl pH 8:0.2 M sodium tetraborate, 2 mM DTT, 5 mM EDTA, 10% (v/v) glycerol, 4% (w/v) insoluble PVPP, 6% (w/v) Amberlite XAD-4, 10 μM leupeptin, 0.2 mM AEBSF, 1 μM pepstatin A, 1 μM Bestatin, 1 μM E-64 and 1 mM 1,10-phenanthroline. The tissue was blended in the extraction buffer for 3 min at maximum speed, filtered through four layers of autoclaved cheesecloth and centrifuged at 20,000 g for 30 min in a refrigerated centrifuge (model J2-HS, Beckman Instruments, Fullerton, Calif.). The supernatant (crude extract) was saved for further purification (see below). An aliquot of the crude extract was desalted by passage through Sephadex G-25 columns (PD10, Amersham Pharmacia, Piscataway, N.J.) prior to assays for total protein and NMTase activities.

Enzyme Assay. The NMTase activities with β-alanine, N-methyl β-alanine and N,N-dimethyl β-alanine were assayed using a radiometric method (Rathinasabapathi et al., Physiol Plant 109:225–231, 2000), with modifications as stated below. The assay mixture contained 54 μL of enzyme preparation in a total volume of 100 μL containing 0.1 M Tris-HCl buffer pH 8.0, 2 mM DTT, 10 mM methyl acceptor, 100 μM AdoMet and 0.027 μM S-Adenosyl-L-[methyl-$^3$H] Met (200 nCi of radioactivity). Following incubation at 30° C. for 30 minutes, the reactions were stopped by the addition of 10 μL of 10% (w/v) trichloroacetic acid containing 1 mM of methylated products as unlabeled carrier. Activated charcoal (38 mg.ml$^{-1}$) in 0.1 N acetic acid, 250 μL per assay, was added and centrifuged for five minutes. The radioactive product in the supernatant was quantified in 75% Ready Gel using a liquid scintillation counter (Beckman Instruments, Fullerton, Calif.). The counting efficiency was 30%.

Enzyme Purification. All protein purification steps were done at 4° C. For column chromatography steps, a low pressure column chromatography system (Bio-Rad, Hercules, Calif.) consisting of a peristaltic pump, UV monitor, a fraction collector and a chart recorder was used. All columns were equilibrated in buffer A (20 mM Tris-HCl pH 8.0, 10% glycerol and 2 mM DTT), prior to use. If required, protein preparations between purification steps were concentrated using a 10 kD cut-off Centriprep (Millipore, Mass.) centrifugal filter device. Protein precipitating between 10% (w/v) and 15% (w/v) PEG 8000 (Fisher Biotech, Fair Lawn, N.J.) was dissolved in buffer A. The NMTase activities were stable in this fraction for at least two months when stored at −80° C. For heat treatment, 25 mL of the PEG-precipitated protein dissolved in buffer A was exposed to 50° C. in a water bath for 15 min. The preparation then was centrifuged at 20,000 g for 20 min and the supernatant was collected. For anion exchange chromatography, protein (about 40 to 50 mg) from the heat treatment step was loaded onto a column (13.5 cm×3 cm) containing 50 mL DEAE-Fractogel EMD ion exchanger (EM Separations Technology, Gibbstown, N.J.). The column was washed with 50 mL buffer A and then with 90 mL buffer A containing 20 mM KCl. The bound proteins were then eluted from the column with 104-mL linear 20 mM to 300 mM KCl gradient in buffer A containing 0.1 mM AEBSF. Fractions (7.5 mL) were collected and assayed for NMTase activities and protein. Fractions with specific activities equal to and above that of the load were pooled and concentrated to 1 to 2 mL prior to gel filtration. Gel filtration was performed on a 70 cm×1.7 cm Sephacryl S-200 HR column (Amersham Pharmacia, Piscataway, N.J.). Fractions (3 mL each) were assayed for NMTase activities and protein, and those with specific activities equal to or above that of the load were pooled. The pooled fractions from the gel filtration step were loaded onto a N,N-dimethyl β-alanine-EAH Sepharose 4B affinity column (5 cm×0.8 cm i.d., 2 mL). The column was washed with buffer A, and with 50 mM KCl. The bound proteins were eluted using buffer A containing 10 mM each of β-alanine and N,N-dimethyl β-alanine and using buffer A containing 200 mM KCl. Substrate elution and the 200 mM KCl elution were pooled and concentrated to 1.3 mL before being loaded on to a continuous electrophoresis prep cell (Model 491, Bio-Rad, Hercules, Calif.). The prep cell used a native-gel column made up of 40 mL of 6% (w/v) acrylamide in 24 mM Tris-CAPS buffer, pH 9.3 (McLellan, 1982). Electrophoresis was at 300 V for 2 h with 24 mM Tris-CAPS buffer, pH 9.3 and the proteins were eluted with buffer A. Fractions (3 mL each) were assayed for NMTase activities and protein. Fractions with specific activities equal to and above that of the load were pooled, concentrated and loaded onto an adenosine agarose affinity gel (3 mL column). Non-specific proteins were washed off the column with buffer A containing 0.2 M KCl and the bound proteins were eluted with 5 mM AdoMet and 0.2 M KCl in buffer A. The eluate was concentrated prior to NMTase and protein assays.

Estimation of Native Molecular Weight. Gel filtration was performed using Sephacryl S-200 column chromatography as described above. The column was calibrated with marker proteins alcohol dehydrogenase (150 kD), bovine serum albumin (66 kD), ovalbumin (45 kD) and cytochrome C (12.4 kD).

Estimation of Protein. Protein was estimated after precipitating it from appropriate volumes of fractions using Lowry's method as modified by Peterson (Anal Biochem 83:346–356, 1977). Bovine serum albumin was used as the standard.

SDS-PAGE. SDS-PAGE was performed according to Laemmli (Nature 227:680–685, 1970) in 12% (w/v) separation gel and 5% (w/v) stacking gel. Proteins were visualized with Coomassie Brilliant Blue or silver-stain.

Estimation of pI. A protein fraction purified about 10-fold was subjected to isoelectric focusing in an IsoGel agarose IEF plate pH 3 to 10 system (FMC Bioproducts, Rockland, Me.) at 1000 V for 40 min. The anolyte was 0.5 M acetic acid pH 2.6 and the catholyte was 1 M NaOH, pH 13. Two lanes in the IEF plate were stained with Coomassie Blue to visualize the proteins and the rest of the agarose gel was sliced into 2 mm strips and assayed for NMTase activities. Maximum activities against all the three methyl acceptors corresponded to pH 5.15 in a standard curve of pIs for known standard proteins focused in the same IEF plate.

Photoaffinity Labeling. To identify the protein subunit(s) binding to AdoMet, photoaffinity labeling (Som and Friedman, J Biol Chem 265:4278–4283, 1990) was done on protein samples at various stages of purification from the ion exchange chromatography stage onward using the method as described by Smith et al., Physiol Plant 108:286–294, 2000.

Kinetic Characterization. A partially-purified enzyme preparation after the anion exchange column chromatography step (Table I) was used. The activity was stable in this fraction when stored at −80° C. for up to two months. The assay procedure and conditions were similar to that described above except that the duration of the assay was reduced to 20 min and the substrate concentrations were varied as indicated. The enzyme concentration employed (15 μg protein per assay) gave a linear reaction velocity during the incubation period. Kinetic constants were derived from the X and Y intercepts of a linear plot of s/v versus s drawn from triplicate assay results. Henderson, P J F (1993) Statistical analysis of enzyme kinetic data. In R. Eisenthal, M J Danson, eds., Enzyme assays a practical approach, IRL Press, Oxford, pp. 276–316. The experiment was repeated twice with similar results.

Effect of a Thiol Reagent. Protein purified using PEG precipitation was assayed with or without added DTT in the presence and absence of the thiol reagent p-hydroxymercuribenzoic acid.

Peptide Sequencing. Purified NMTase (400 ng) was separated by SDS-PAGE and stained with Coomassie R-250 and destained in 10% (v/v) methanol and 5% (v/v) acetic acid. The band of protein was digested by endoproteinase Lys-C, separated in an HPLC and sequenced using Edman degradation. Rosenberg I M (1996) Peptide mapping and microsequencing. In Protein analysis and purification. Birkhauser, Boston, pp. 183–206. The peptide sequences were compared to other proteins in the databases using the BLAST program. Altschul et al., Nucleic Acids Res 25:3389–3402, 1997.

Example 2

Results

Peptide Studies. Because *L. latifolium* leaves are rich in phenolics, the enzyme purification protocol employed non-ionic polymeric adsorbent XAD4, polyvinyl polypyrrolidone PVPP (Loomis, Methods in Enzymol 31:528–544, 1974), and protease inhibitors in the extraction medium and elution buffers used in early chromatography steps. A series of steps were employed to purify the NMTase as detected by assays with β-alanine, N-methyl β-alanine and N,N-dimethyl β-alanine (Table I). Each step was found to improve NMTase specific activities in smaller scale trials. However, when scaled up, certain steps did not reproducibly improve purity (Table I, heating and Sephacryl S-200 column chromatography for example).

Figure 2:
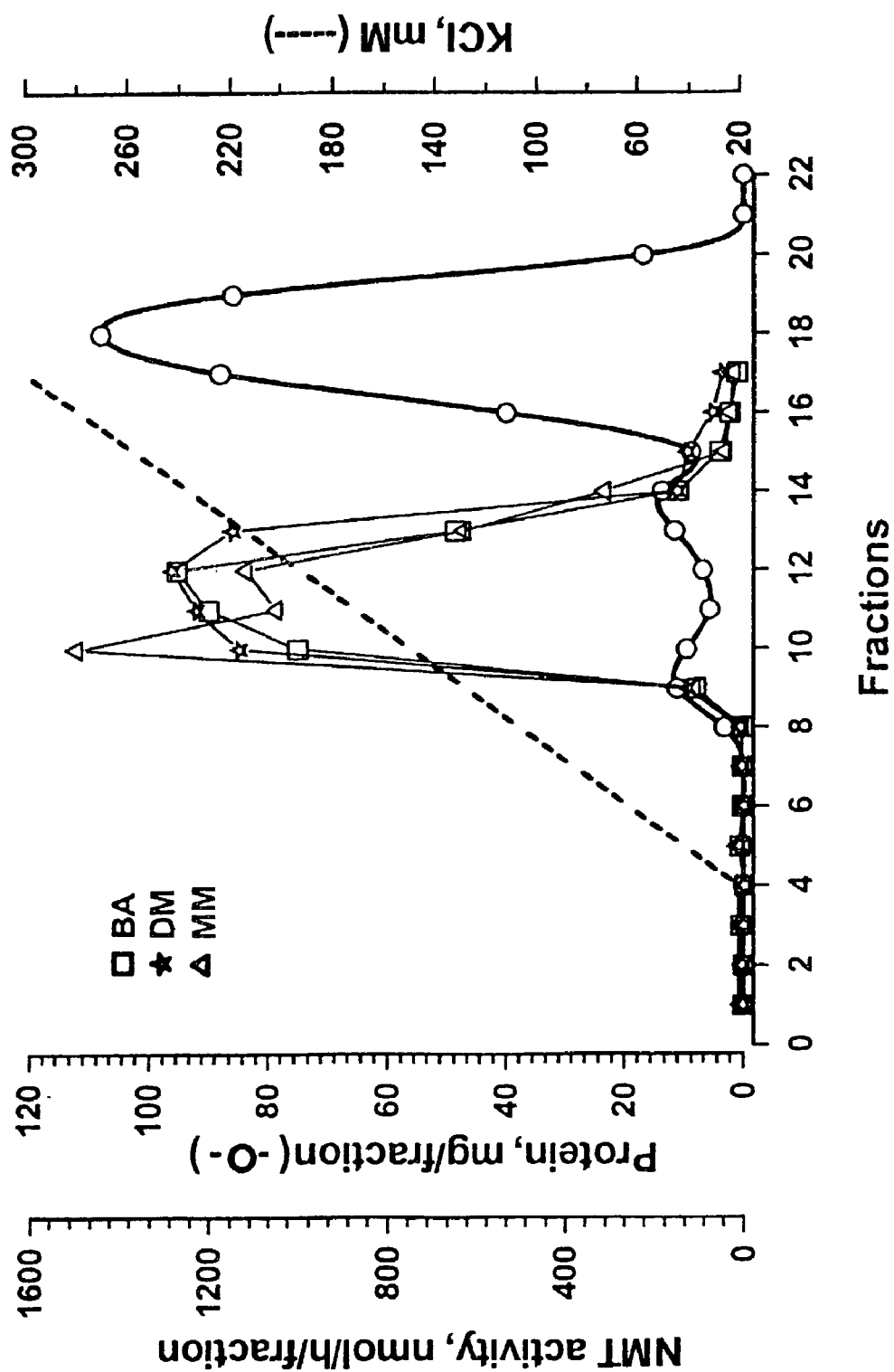
FIG. 2 is a graph showing the NMTase activity and protein amounts in fractions separated by anion exchange chromatography using DEAE-Fractogel. The procedure is described in the methods section. NMTase activities (nmol $h^{-1}$/fraction) against β-alanine (BA), N-methyl β-alanine (MM) and N,N-dimethyl β-alanine (DM) are indicated by squares, triangles and stars, respectively. The predicted KCl gradient (20 to 300 mM) is shown in a dotted line. Protein content (mg/fraction), estimated by the modified Lowry's method (Peterson et al., Anal Biochem 83:346–356, 1977) is shown in open circles.

PEG precipitation step was employed primarily to concentrate the extracted protein in a stable form, achieving a 2-fold purification. In separate trials, heat treatment of the PEG fraction resulted in 2-fold improvement in specific activities. DEAE-Fractogel anion exchange column chromatography improved specific activities to about 6-fold (Table I) as shown in FIG. 2. NMTase activities eluted from DEAE-fractogel column between 125 mM and 200 mM KCl, ahead of the majority of proteins (FIG. 2).

Following anion exchange chromatography, the protein fraction was purified by gel filtration chromatography on Sephacryl S-200. NMTase activity eluted as a single peak with an elution volume corresponding to a native molecular weight of 80 kD. The use of protease inhibitors proved extremely valuable in this step. Without inhibitors, NMTase activity eluted in four peaks corresponding to 110, 80, 40 and 20 kD, the 80 kD NMTase being more than 50% of the total recovered activity, and the total activity recovered was substantially reduced. Activity at 110 kD was probably due to protein aggregation.

Figure 3:
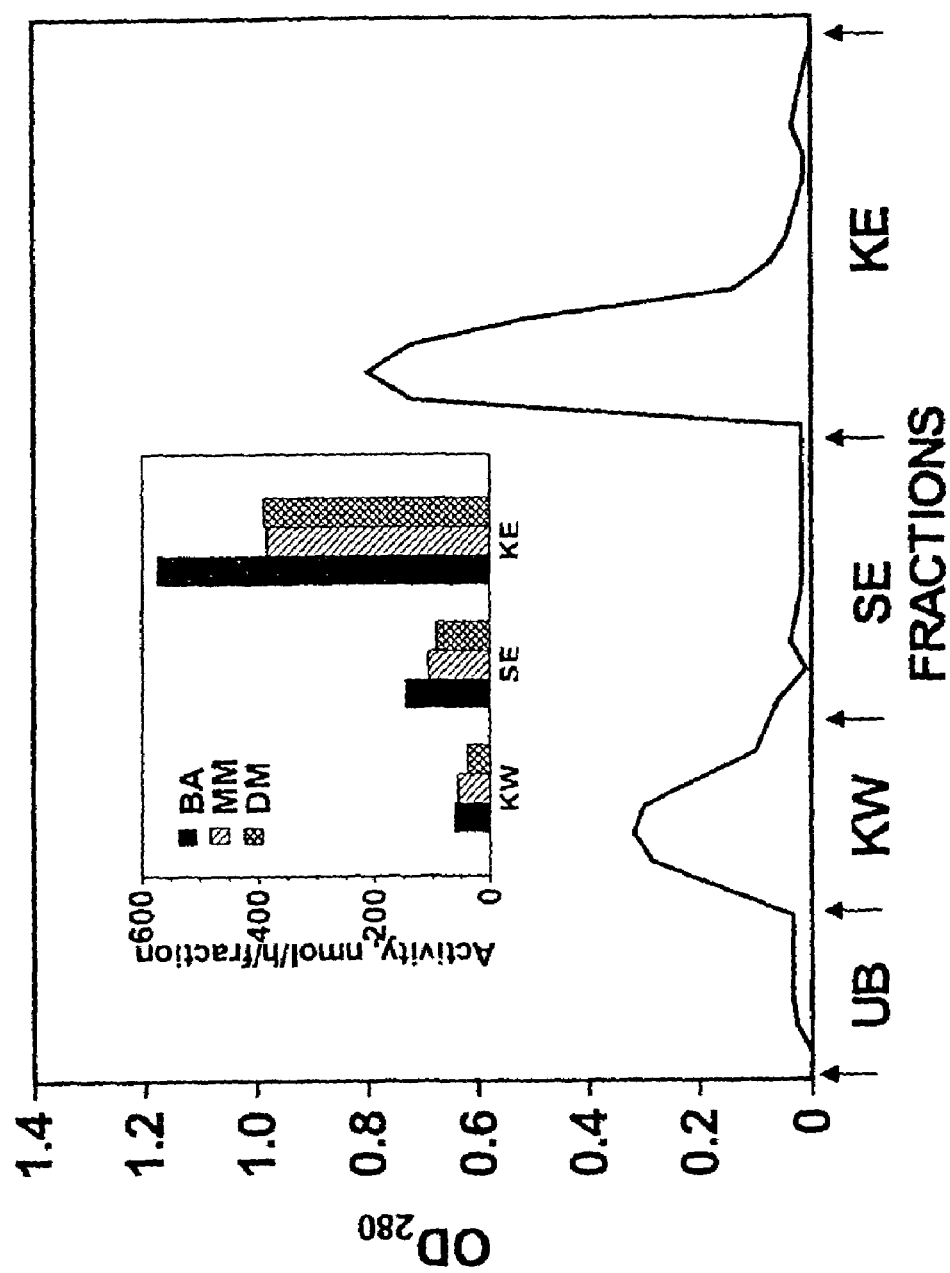
FIG. 3 is a graph showing the NMTase activity and protein concentrations in fractions separated by N,N-dimethyl β-alanine substrate affinity column chromatography. Protein elution profile by $OD_{280}$ is shown for the unbound fraction (UB) and elutions (KW=50 mM KCl wash, SE=substrate elution and KE=200 mM KCl elution). NMTase activities (nmol $h^{-1}$/fraction) with β-alanine (BA), N-methyl β-alanine (MM) and N,N-dimethyl β-alanine (DM) measured in the wash and the elutions are shown in the inset.

N,N-Dimethyl β-alanine-EAH sepharose affinity matrix bound most proteins loaded (FIG. 3). β-alanine and N,N-Dimethyl β-alanine at 10 mM each were not sufficient to elute most NMTase activities from this column. Elution with 200 mM KCl was more effective (FIG. 3, inset), suggesting that the matrix also had anion exchange characteristics in addition to affinity features.

Figure 4:
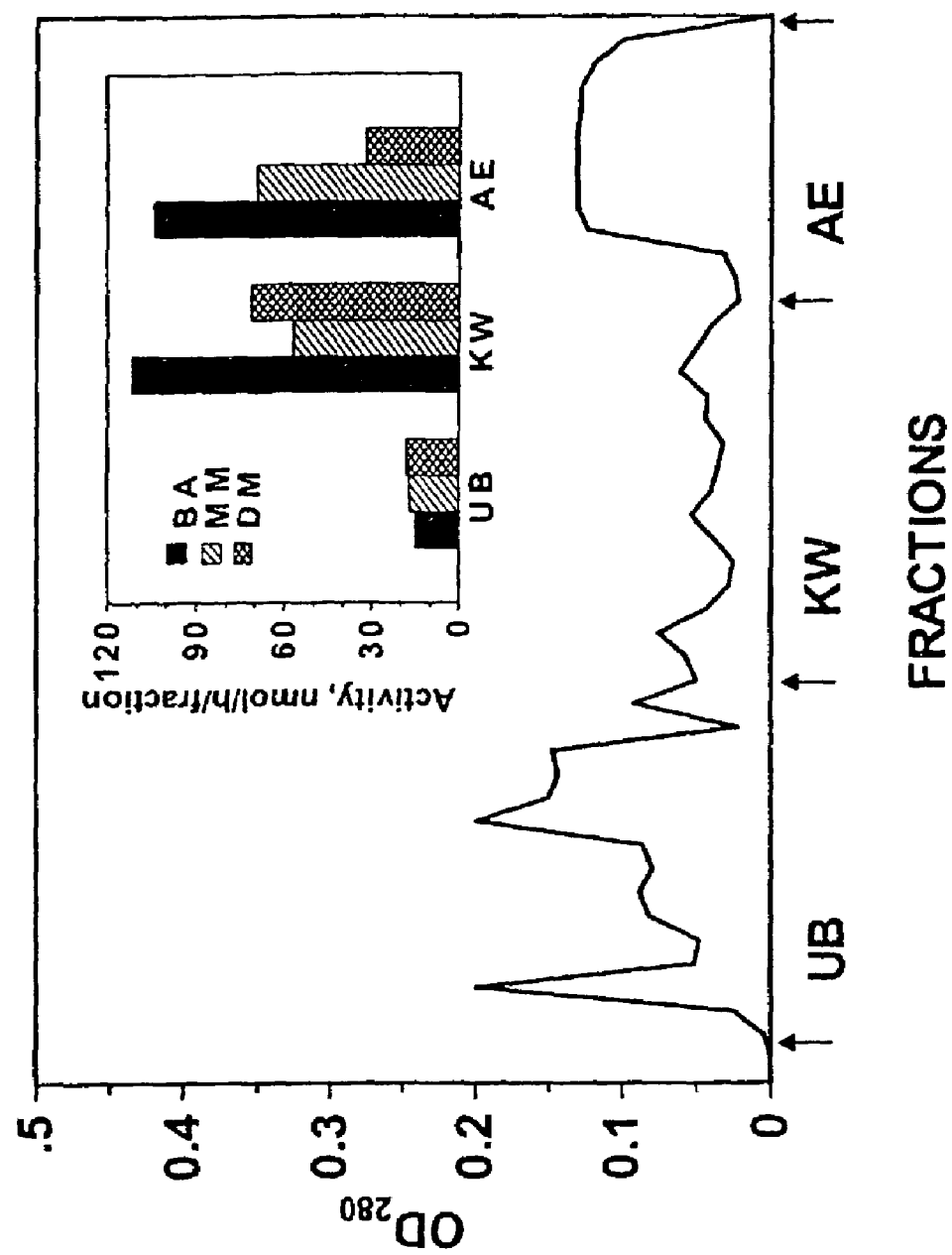
FIG. 4 is a graph showing the NMTase activity and protein concentrations in fractions separated by adenosine agarose affinity chromatography. Protein elution profile by $OD_{280}$ Of fractions is shown for unbound (UB), 200 mM KCl wash (KW) and substrate elution with 5 mM AdoMet (AE). Note that absorbance in the AdoMet elution is largely due to the AdoMet and not protein. NMTase activities (nmol $h^{-1}$/fraction) with β-alanine (BA), N-methyl β-alanine (MM) and N,N-dimethyl β-alanine (DM) measured in the unbound fraction, 200 mM KCl wash and AdoMet elution are shown in the inset.
Figure 5:
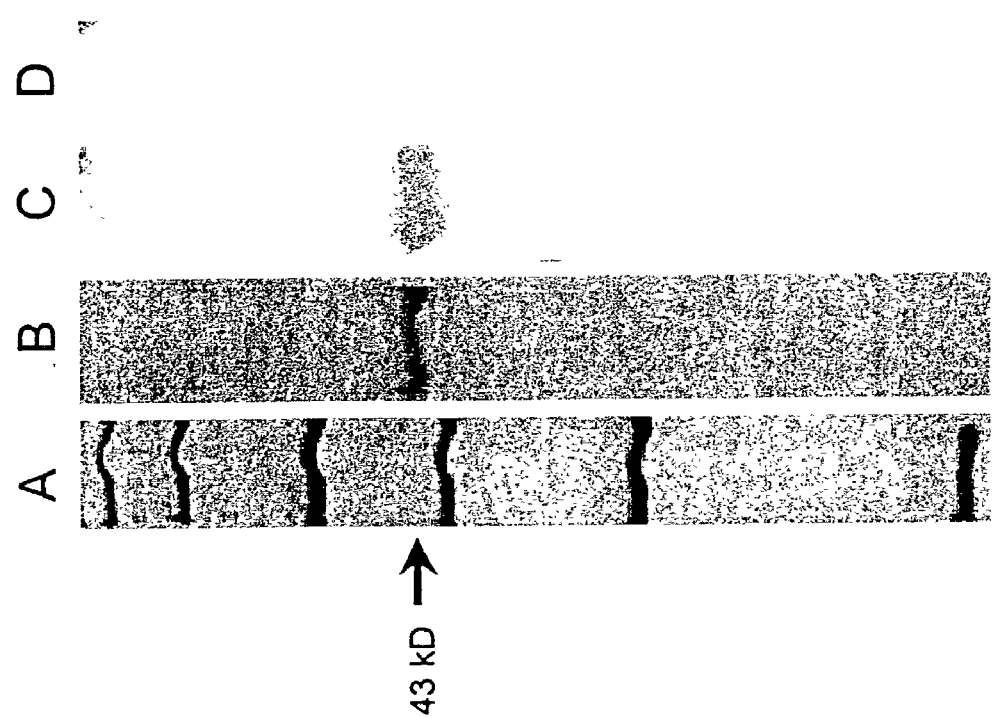
FIG. 5 is an autoradiograph of a gel from SDS-PAGE analysis of the purified L. latifolium NMTase and Photoaffinity labeling. Lane A: Precision SDS-Protein markers (Bio-Rad 161–0362). Lane B: SDS-Denatured protein (20 ng) from the adenosine agarose step (Table I), separated in a 12% acrylamide gel and stained with silver stain. Lane C: Partially purified (100-fold) NMTase fraction following photoaffinity labeling with S-Adenosyl-L-[methyl-$^3$H]Met, SDS-PAGE and autoradiography. Lane D: Partially purified (100-fold) NMTase fraction following photoaffinity labeling with S-Adenosyl-L-[methyl-$^3$H]Met in the presence of AdoHCy, SDS-PAGE and autoradiography.

Continuous elution gel electrophoresis using a Prep Cell improved specific activities about 34 fold (Table I). From this step onward, however, the enzyme was labile and the steps needed to be performed without interruption. In the buffer system employed, the NMTase activities eluted six to nine mL after the dye front eluted. Adenosine agarose effected about a 1890-fold increase in specific activities (FIG. 4). The purified fraction methylated β-alanine, N-methyl β-alanine, and N,N-dimethyl β-alanine (Table I). However, the specific activities observed using N-methyl β-alanine and N,N-dimethyl β-alanine as substrates were less than those observed using β-alanine (Table I). The enzyme was labile in this fraction, especially for the activity against N,N-dimethyl β-alanine, with about 50% loss of activity over 12 h on ice. SDS-PAGE analysis indicated that the purified protein fraction had one major protein at about 43 kD (FIG. 5, lane B). There were minor contaminants at around 66 kD, appearing as a faint doublet in a silver-stained gel (FIG. 5, lane B). Storage of the purified protein at −80° C. resulted in the generation of a protein band at around 25 kD. The amount of this 25 kD product increased as the storage period increased.

When a partially purified protein fraction was subjected to photoaffinity labeling with S-adenosyl-L-[methyl-$^3$H]Met, the 43 kD protein was labeled (FIG. 5, lane C). When S-adenosyl-L-homocysteine (AdoHCy) at 217 µM was added prior to crosslinking, the photoaffinity labeling was completely inhibited (FIG. 5, lane D). Experiments showed that the 43 kD affinity-labeled subunit was degrading during storage producing a labeled band about 25 kD size.

Figure 6:
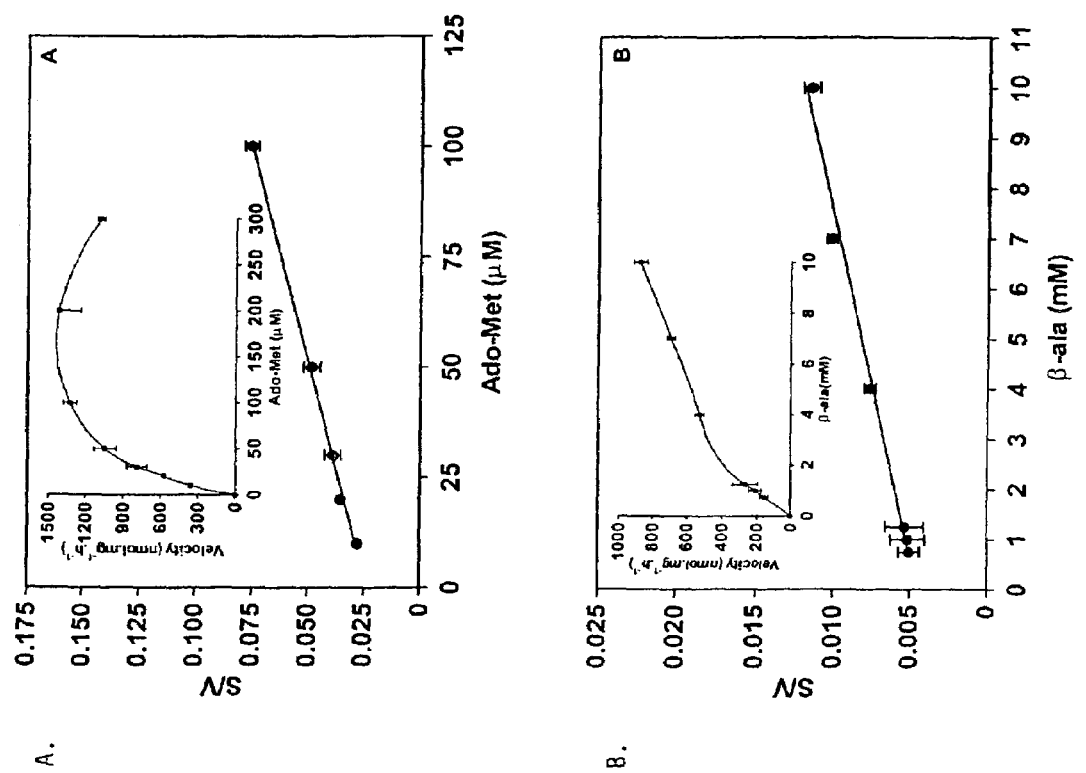
FIG. 6 illustrates two graphs showing the results of a kinetic analysis of L. latifolium NMTase protein. (A) Effect of varying Ado-Met concentration on the reaction velocity shown in a plot of s/v versus s. Ado-Met concentration was varied from 0 to 300 μM and β-alanine concentration was kept at 10 mM. Inset shows the direct plot. (B) Effect of varying β-alanine on the reaction velocity shown in a plot of s/v versus s. β-alanine levels were varied between 0 and 10 mM. Ado-Met concentration was kept at 100 μM.

The reactions catalyzed by the NMTase exhibited Michaelis-Menten kinetics with respect to its substrate saturation response. The response for varying Ado-Met and β-alanine are shown in FIG. 6. Similar plots for N-methyl β-alanine and N,N-dimethyl β-alanine were employed to derive the kinetic parameters listed in Table II. At 10 mM β-alanine, Ado-Met exhibited substrate inhibition above 200 µM (FIG. 6A). Apparent Km for Ado-Met was 45 µM. Apparent Km for the methyl acceptor substrates determined at 100 µM Ado-Met were around 5 mM (Table II). The catalytic efficiency, $V_{max}/K_m$ values were comparable for the three methyl acceptors (Table II). AdoHCy was highly inhibitory to the NMTase: 50% inhibition was achieved at 40 µM AdoHCy at 10 mM β-alanine and 100 µM Ado-Met.

Isoelectric focusing (IEF) experiments indicated a single peak of activity at a pI of 5.15. The sulfhydral reagent p-hydroxymercuribenzoic acid highly inhibited the NMTase (Table III). This inhibition was partially reversible by DTT suggesting that cysteines are involved in the active site of the NMTase.

Example 3

Cloning of the β-alanine NMTase cDNA

Total RNA was extracted from leaves using a modified hot borate method. Briefly, leaves were ground in a mortar in liquid nitrogen and DTT powder (2 mM final concentration) and were further extracted in a boiling medium containing 0.2 M sodium borate, 30 mM EDTA and 1% (wt/v) sodium dodecyl sulfate (SDS), pH 9. Proteins were digested using proteinase K (5 mg per g fresh weight tissue) at 42E C for 2 h. SDS was removed by precipitation by the addition of potassium chloride solution to a final concentration of 145 mM. The extract was then filtered through four layers of cheese cloth and centrifuged 20,000 g. Barium chloride at 75 mM was added to the supernatant to remove carbohydrates. Following this step, lithium chloride at 2M was used to precipitate the total RNA. Lithium chloride step was repeated two more times to achieve high purity total RNA. The RNA was concentrated by precipitation in ethanol, redissolved in RNAse-free water, quantified using a UV-visible spectrophotometer and analyzed by gel electrophoresis. Poly A+ RNA was isolated from the total RNA using Oligo dT-cellulose (GenElute-mRNA miniprep kit, Sigma Chemical Co., St. Louis, Mo.). First strand cDNA was synthesized using oligo (dT)$_{20}$ primers and reverse transcriptase (Thermoscript RT-PCR System, Life Technologies).

Active β-alanine N-methyltransferase protein was purified from leaves of L. latifolium using the procedure described previously (Rathinasabapathi et al., Plant Physiol. 126:1241–1249, 2001). The purified protein (20 µg) was separated on an SDS-PAGE gel and stained with Coomassie Blue. The 43 kDa band was eluted from the gel and digested with LysC. Peptide sequencing was done by Edman degradation (Tempst et al., Electrophoresis 11:537–553, 1990). Based on the peptide sequences degenerate primers were designed for RT-PCR. Each primer included one or two inosines.

Degenerate primers were designed based on the peptides 1, 2 and 3 in both sense (F) and antisense (R) orientations (Table IV). Under optimum conditions, primers 2F and 3R amplified a 500 bp cDNA. Primer combinations 2F and 1R and 1F and 3R produced shorter products of 400 bp and 100 bp respectively. The 500 bp PCR product was named clone 23 and sequenced. The DNA sequence of clone 23 is shown herein as SEQ ID NO:20.

RT-PCR was performed using a RT-PCR kit (Thermoscript RT-PCR system, In Vitrogen, Carlsbad, Calif.) according to manufacturer's instructions. RT-PCR reactions were in a volume of 50 µL in thin walled amplification tubes. The reactions contained 10 µL of first strand reaction, 200 µM of each of the four dNTPs, 2 mM of magnesium chloride, 4 µM each of the sense and antisense primers, 5 units of Taq DNA polymerase in 10 mM Tris-HCl pH 9, 50 mM KCl and 0.1% Triton X-100. Forty cycles each with 93° C. for 30 sec for denaturation, 60° C. for 30 sec for annealing and 72° C. for 1.5 min for extension, were performed in a thermal cycler (MiniCycler, MJ Research Corp.). The products were analyzed in an 1% agarose gel and stained with ethidium bromide. The sequence shown herein as SEQ ID NO:21 is a PCR product obtained using SEQ ID NO:23 as a primer.

cDNA Library Construction. Poly A+ RNA was isolated from L. latifolium leaves from plants salinized with 200 mM NaCl. First and second strand cDNAs were made using M-MLV reverse transcriptase (Sambrook et al., supra). cDNAs size-selected for 1000 bp were cloned into the EcoRI site of lambda vector gt10 (Clontech, Palo Alto, Calif.). The primary library had a titer of 1.5×10$^6$ plaque forming units per mL.

Library Screening. Clone 23 was labeled with $^{32}$PdGTP (800 Ci per mmol, Amersham BioSciences, Piscataway, N.J.) using a random primer labeling kit (In Vitrogen, Carlsbad, Calif.) according to manufacturer's instructions. Plaque lifts of the library on nylon membranes were screened using the radiolabeled probe by following the formamide procedure (Sambrook et al., supra). Positive clones were identified following autoradiography and purified using standard protocols (Sambrook et al., supra). Lambda DNA was extracted using Wizard Lambda prep system (Promega, Madison, Wis.) according to manufacturer's protocol.

DNA Sequencing and Analysis. DNA sequencing was in both strands using the fluorescent chain terminating dideoxynucleotides method. DNA sequences were analyzed by several software packages including BLAST (Patnaik and Blumenfeld, Anal. Biochem. 289:1–9, 2001).

Partial cDNA clones represented two groups, NMTase A (SEQ ID NOs:25–27) and NMTase B (SEQ ID NO: 24) differing only in their 3' untranslated region. The full-length (1414 bp) NMTase A cDNA, reconstructed by splicing clone gt61 to the 5'R ACE product (SEQ ID NO:22), had 119 bp of 5' untranslated region, an open reading frame of 1125 bp and a 3' untranslated region of 167 bp (FIG. 7A). The open reading frame had two ATGs within the first 30 bp. The sequence context near the first methionine had matched well with the sequence context conserved around the initiation codon for plant genes. Joshi Nucleic Acid Res 15: 6643–6653, 1987; Cavener and Ray, Nucleic acid Res 19: 3185–3192, 1991. A putative polyadenylation signal, AAATAAT preceded poly A+ by 17 bp (FIG. 7A). Heidecker and Messing, Annu Rev Plant Physiol Plant Mol Biol 37: 439–466, 1986.

The deduced amino acid sequence had 375 amino acid residues (FIG. 7B) resulting in a theoretical mass of 41,286 Da and a pI of 5.84, closely resembling experimental determinations of 43 kDa and 5.15. Rathinasabapathi et al., Plant Physiol 126: 1241–1249, 2001. The deduced amino acid sequence had all the peptides that were sequenced (see peptide sequences below) from purified β-alanine NMTase (FIG. 7B). All the three motifs implicated in S-adenosyl-l-methionine binding were conserved in β-alanine NMTase. Joshi and Chiang, Plant Mol Biol 37: 663–674, 1998. The deduced amino acid sequence showed high sequence homology to caffeic acid O-methyltransferases and related O-methyltransferases. For example β-alanine NMTase had 53% identity and 72% homology to alfalfa O-diphenol-O-methyltransferase (E.C. 2.1.1.6). Sequence relatedness to O-methyltransferases suggests the possibility of β-alanine NMTase having phylogenetic relations to O-methyltransferases. There is no recognizable signal sequence based upon sequence analyses, suggesting that b-alanine methylation occurs in the cytoplasm. Emanuelsson et al., J Mol Biol 300: 1005–1016, 2000.

RNA Blots. Total RNA from *L. latifolium* and *L. sinuatum* were loaded onto a formaldehyde agarose (1.2% wt/v) gel, 10 mg per lane and blotted onto nylon membranes (Sambrook et al., supra). Equal loading of RNA in the gels was verified by ethidium bromide staining of the gel. Completion of RNA transfer was verified by methylene blue staining of the blots. The blots were probed using clone 23 cDNA probe labeled with $^{32}$P dGTP. Band intensity in autoradiographs were analyzed using densitometry. Results indicated that NMTase mRNA is expressed in *L. latifolium* leaves but not in the leaves of *L. sinuatum*, a species that does not methylate β-alanine. Hanson et al., Plant Physiol 97: 1199–1205, 1991.

Specific expression of mRNA in a β-alanine betaine accumulator, the presence of peptide sequences that were obtained experimentally from purified β-alanine NMTase protein, and the sequence homology to other methyltransferases were consistent with the assertion that the isolated cDNA clone codes for β-alanine NMTase.

Peptide sequences were obtained from the purified NMTase protein from *L. latifolium* (Sequences A–H below). Amino acids in parentheses are alternate possibilities arising from ambiguities in sequencing.

Sequence A
H(S/Q/A) R T E(Q) E E (L) Y R Q L G L L A G (SEQ ID NO:1)

Sequence B
S(Q/A) L D G (A) S G (Y/E) D G F E G (SEQ ID NO:2)

Sequence C
S(R/H/A/Q)R T E E E Y R Q L G L L A G(SEQ ID NO:3)

Sequence D
A L L G S G Y D G F E G V K (SEQ ID NO:4)

Sequence E
F R V I H V D Y F F P V V E F (SEQ ID NO:5)

Sequence F
H (S/A/Q)RTE(Q)EE(L)YRQLGLLAG (SEQ ID NO:9)

Sequence G
AVI(P)ELXTAILDA(K)S (SEQ ID NO:10)

Sequence H
R(H/A/Q)INFDLPXVVA (SEQ ID NO:11)

In a BLAST search, Sequence A shared some homology with the peptide sequences of several other methyltransferases (see below), but Sequence B did not. Sequence A showed homology to:

a. Caffeic acid O-methyltransferase-like protein of *Arabidopsis thaliana* emb|CAB64217.1 Sequence matched: 325 HRTEEEFIELGLSAG (SEQ ID NO:6)339;

b. Putative DNA enzyme of *Eikenella corrodens* gb|AAD18127.1 Sequence matched: 154 EYRQLGLLA (SEQ ID NO:7)162; and c. O-diphenol-O-methyltransferase of *Medicago sativa* subsp. varia. Emb|CAB65279.1 Sequence matched 324 HRTEEQFKQLG (SEQ ID NO:8) 334.

Example 4

Expression in Yeast

The open reading frame for the β-alanine NMTase was amplified using primers 5' to 3' gcggatccaatggcgaaccactcctcagctg (SEQ ID NO:30) and 5' to 3' ctcgagtcacttctggaactctaccacgg (SEQ ID NO:31) and *L. latifolium* cDNA was the template. These primers were designed with an add-on containing BclI and XhoI restriction sites. The amplified 1143 bp product was subcloned into pCR2.1 TOPO vector. A BamHI/XhoI fragment containing the cDNA was directionally cloned in frame in the yeast expression vector pYES NT-C (InVitrogen, Carlsbad, Calif.). The plasmid was introduced into *Saccharomyces cerevisiae* InVSc strain by a LiCl procedure (Ausubel et al., 1995). The recombinant protein, as a hexa-histidine fusion protein on its N-terminus was purified using the nickel affinity column as per manufacturer's instructions. The purified protein was subjected to enterokinase cleavage and assayed for N-methyltransferase activities using the radiometric method described previously (Rathinasabapathi et al., Plant Physiol. 126:1241–1249, 2001).

Example 5

Expression in Tobacco

A full-length EDNA for β-alanine N-methyltransferase was subcloned into the EcoRI site of pMON979-R5 vector under the control of a modified Cauliflower mosaic virus 35S promoter. The recombinant vector pR5-NMT was transferred into *Agrobacterium tumefaciens* strain ABI via triparental mating (Walkerpeach and Velten, Plant Molecular Biology Manual B1:1–19, 1994). Transformation of tobacco by *Agrobacterium* was achieved by leaf disk procedure (Horsch et al., Science 227:1229–1231, 1985). Putative transformants were identified based on their kanamycin resistance.

Transgenic plants were analyzed for the expression of β-alanine NMTase using PCR, RNA blots, immunoblots and enzyme assays. Transgenic plants were then transferred to a greenhouse and seeds were collected following selfing.

Example 6

Test for Stress Tolerance

To test the effect of salinity tolerance, vector alone control and β-alanine N-methyltransferase transformants were grown in vermiculite irrigated daily with a half-strength Hoagland solution. After a two-week period, NaCl was included at 50 mM increments for every three days until reaching 200 mM NaCl. The plants were harvested and leaves, stem and roots were dissected and weighed. Growth data were analyzed using analysis of variance comparing fresh weight and dry weight increases during the experimental period for the vector alone control and β-alanine NMTase transformants.

TABLE I

Purification of an AdoMet dependent NMTase from 550 g fresh weight leaves of L. latifolium. Fold-purification was calculated based on specific activities measured with β-alanine.

| Step | Total protein (mg) | Specific Activity nmol · h · mg protein | | | Fold purification |
| --- | --- | --- | --- | --- | --- |
| | | β-alanine | N-methyl β-alanine | N,N-dimethyl β-alanine | |
| Crude | 2533.3 | 8.3 | 8.1 | 12.8 | 1 |
| 10–15% PEG | 1315.2 | 16.6 | 6.3 | 8.1 | 2 |
| Heating | 1156.2 | 15.3 | 12 | 13.2 | 2 |
| DEAE-Fractogel | 46.8 | 47.3 | 39.9 | 40.7 | 6 |
| Sephacryl S-200 | 11.3 | 46 | 38 | 32 | 6 |
| N,N-dimethyl β-alanine: Sepharose | 5.1 | 104 | 71 | 70 | 13 |
| Prep Cell electrophoresis | 0.65 | 285.3 | 185.4 | 174.8 | 34 |
| Adenosine Agarose | 0.004 | 15690 | 9020 | 4195 | 1890 |

TABLE II

Kinetic parameters of NMTase from L. latifolium leaves. Replots of data from substrate response experiments were used to determine the value of the kinetic parameters.

| Substrate | Apparent Km (mM) | Vmax (nmol · mg · h) | Vmax/Km Catalytic efficiency |
| --- | --- | --- | --- |
| β-alanine | 5.28 | 1216 | 230 |
| N-methyl β-alanine | 5.68 | 1290 | 227 |
| N,N-dimethyl β-alanine | 5.87 | 1697 | 289 |
| Ado-Met | 0.045 | 1922 | 43094 |

TABLE III

Inhibition of L. latifolium NMTase by p-hydroxymercuribenzoate.

| Treatment | % Activity BA | % Activity MM | % Activity DM |
| --- | --- | --- | --- |
| Control, 5 mM DTT in the assays | 100 ± 4.6 | 100 ± 6.2 | 100 ± 11.4 |
| Minus DTT | 59.2 ± 1.1 | 58.7 ± 1.3 | 87.3 ± 16.0 |
| Minus DTT Plus 0.2 mM pHMB | 1.3 ± 0.7 | 2.4 ± 1.4 | 0.4 ± 0.2 |
| 0.2 mM pHMB 10 min + 5 mM DTT for 30 min. | 22.6 ± 2.9 | 23.0 ± 2.9 | 55.2 ± 7.6 |

Activities are expressed as per cent total relative to control assays containing 5 mM DTT. They were assayed, 30 min total time in each case, against β-alanine (BA), N-methyl β-alanine (MM) and N,N-dimethyl β-alanine (DM) as described in the methods. Values are means and standard errors from three determinations.
pHMB = p-hydroxymercuribenzoate.

TABLE IV

Degenerate Primer Sequences used for RT-PCR.

Primer Name Sequence (5' to 3') I is inosine.

| | | |
| --- | --- | --- |
| 1F | CAYMGIACYGARGARGARTAYMG | (SEQ ID NO: 12) |
| 1R | TGICKRTAYTCYTCYTCIGT | (SEQ ID NO: 13) |
| 2F | GGITAYGAYGGITTYGARGGIGT | (SEQ ID NO: 14) |
| 2R | TTIACICCYTCRAANCCRTC | (SEQ ID NO: 15) |
| 3F | ATHCAYGTIGAYTAYTTYTTYC | (SEQ ID NO: 16) |
| 3R | ACIGGRAARAARTARTCIACRTG | (SEQ ID NO: 17) |
| 23R | CCACCAACATCTACCAATG | (SEQ ID NO: 18) |
| 4F | ACIGCNATHYTIGAYGCIWS | (SEQ ID NO: 19) |

Primers were named for the peptide they were derived.
F stands for forward and R for reverse direction of the primers.

Other Embodiments

While the above specification contains many specifics, these should not be construed as limitations on the scope of the invention, but rather as examples of preferred embodiments thereof. Many other variations are possible. Therefore to apprise the public of the scope of the invention and the embodiments covered by the invention, the following claims are made.

What is claimed is:

1. A purified nucleic acid comprising a nucleotide sequence that encodes a protein that:
   (a) is identified by SEQ ID NO:29; and
   (b) has at least one functional activity of a native *Limonium latifolium* N-Methyltransferase.

2. A purified nucleic acid wherein the nucleic acid encodes a protein that comprises SEQ ID NO: 29.

3. A vector comprising a nucleic acid encoding a protein that:
   (a) is identified by SEQ ID NO: 29; and
   (b) has at least one functional activity of a native *Limonium latifolium* N-Methyltransferase.

4. The vector of claim 3, wherein said nucleic acid is operably linked to one or more expression control sequences.

5. The vector of claim 4, wherein the one or more expression control sequences comprises a promoter.

6. A cell into which has been introduced the nucleic acid of claim 1.

7. The cell of claim 6, wherein the cell is a plant cell.

8. The cell of claim 7, wherein the plant cell is in a plant.

* * * * *

UNITED STATES PATENT AND TRADEMARK OFFICE
CERTIFICATE OF CORRECTION

PATENT NO.       : 7,202,084 B2  
APPLICATION NO.  : 10/213473  
DATED            : April 10, 2007  
INVENTOR(S)      : Rathinasabapathi et al.

Page 1 of 1

It is certified that error appears in the above-identified patent and that said Letters Patent is hereby corrected as shown below:

Title Page, Item (75) Inventors: Change "Badu" to --Babu--

Title Page, Item (57) ABSTRACT: On line 1, change "*Lumonium*" to --*Limonium*--

Column 4, line 7: Change both occurrences of "β-alanaine" to --β-alanine--

Column 4, line 8: Change "β-alanaine" to --β-alanine--

Column 30, line 38: Change "EDNA" to --cDNA--

Signed and Sealed this

Twenty-first Day of August, 2007

JON W. DUDAS  
*Director of the United States Patent and Trademark Office*

SEQUENCE LISTING

<160> NUMBER OF SEQ ID NOS: 31

<210> SEQ ID NO 1
<211> LENGTH: 20
<212> TYPE: PRT
<213> ORGANISM: Limonium latifolium
<220> FEATURE:
<221> NAME/KEY: UNSURE
<222> LOCATION: (8)..(8)
<223> OTHER INFORMATION: Residue 8 is an alternate possibility arising
      from ambiguities in sequencing.

```
<220> FEATURE:
<221> NAME/KEY: UNSURE
<222> LOCATION: (2)..(4)
<223> OTHER INFORMATION: Residues 2-4 are alternate possibilities
      arising from ambiguities in sequencing.
<220> FEATURE:
<221> NAME/KEY: UNSURE
<222> LOCATION: (11)..(11)
<223> OTHER INFORMATION: Residue 11 is an alternate possibility arising
      from ambiguities in sequencing.

<400> SEQUENCE: 1

His Ser Gln Ala Arg Thr Glu Gln Glu Glu Leu Tyr Arg Gln Leu Gly
1               5                   10                  15

Leu Leu Ala Gly
            20

<210> SEQ ID NO 2
<211> LENGTH: 16
<212> TYPE: PRT
<213> ORGANISM: Limonium latifolium
<220> FEATURE:
<221> NAME/KEY: UNSURE
<222> LOCATION: (7)..(7)
<223> OTHER INFORMATION: Residue 7 is an alternate possibility arising
      from ambiguities in sequencing.
<220> FEATURE:
<221> NAME/KEY: UNSURE
<222> LOCATION: (2)..(3)
<223> OTHER INFORMATION: Residues 2-3 are alternate possibilities
      arising from ambiguities in sequencing.
<220> FEATURE:
<221> NAME/KEY: UNSURE
<222> LOCATION: (10)..(11)
<223> OTHER INFORMATION: Residues 10-11 are alternate possibilities
      arising from ambiguities in sequencing.

<400> SEQUENCE: 2

Ser Gln Ala Leu Asp Gly Ala Ser Gly Tyr Glu Asp Gly Phe Glu Gly
1               5                   10                  15

<210> SEQ ID NO 3
<211> LENGTH: 19
<212> TYPE: PRT
<213> ORGANISM: Limonium latifolium
<220> FEATURE:
<221> NAME/KEY: UNSURE
<222> LOCATION: (2)..(5)
<223> OTHER INFORMATION: Residues 2-5 are alternate possibilities
      arising from ambiguities in sequencing.

<400> SEQUENCE: 3

Ser Arg His Ala Gln Arg Thr Glu Glu Glu Tyr Arg Gln Leu Gly Leu
1               5                   10                  15

Leu Ala Gly

<210> SEQ ID NO 4
<211> LENGTH: 14
<212> TYPE: PRT
<213> ORGANISM: Limonium latifolium

<400> SEQUENCE: 4

Ala Leu Leu Gly Ser Gly Tyr Asp Gly Phe Glu Gly Val Lys
1               5                   10

<210> SEQ ID NO 5
<211> LENGTH: 15
<212> TYPE: PRT
<213> ORGANISM: Limonium latifolium
```

-continued

```
<400> SEQUENCE: 5

Phe Arg Val Ile His Val Asp Tyr Phe Phe Pro Val Val Glu Phe
1               5                   10                  15

<210> SEQ ID NO 6
<211> LENGTH: 20
<212> TYPE: PRT
<213> ORGANISM: Limonium latifolium
<220> FEATURE:
<221> NAME/KEY: UNSURE
<222> LOCATION: (2)..(4)
<223> OTHER INFORMATION: Residues 2-4 are alternate possibilities due to
      ambiguities in sequencing.
<220> FEATURE:
<221> NAME/KEY: UNSURE
<222> LOCATION: (8)..(8)
<223> OTHER INFORMATION: Residue 8 is an alternate possibility due to
      ambiguities in sequencing.
<220> FEATURE:
<221> NAME/KEY: UNSURE
<222> LOCATION: (11)..(11)
<223> OTHER INFORMATION: Residue 11 is an alternate possibility due to
      ambiguities in sequencing.

<400> SEQUENCE: 6

His Ser Ala Gln Arg Thr Glu Gln Glu Glu Leu Tyr Arg Gln Leu Gly
1               5                   10                  15

Leu Leu Ala Gly
            20

<210> SEQ ID NO 7
<211> LENGTH: 15
<212> TYPE: PRT
<213> ORGANISM: Limonium latifolium
<220> FEATURE:
<221> NAME/KEY: UNSURE
<222> LOCATION: (4)..(4)
<223> OTHER INFORMATION: Residue 4 is an alternate possibility due to
      ambiguities in sequencing.
<220> FEATURE:
<221> NAME/KEY: MISC_FEATURE
<222> LOCATION: (7)..(7)
<223> OTHER INFORMATION: residue X is unknown
<220> FEATURE:
<221> NAME/KEY: UNSURE
<222> LOCATION: (14)..(14)
<223> OTHER INFORMATION: Residue 14 is an alternate possibility due to
      ambiguities in sequencing.

<400> SEQUENCE: 7

Ala Val Ile Pro Glu Leu Xaa Thr Ala Ile Leu Asp Ala Lys Ser
1               5                   10                  15

<210> SEQ ID NO 8
<211> LENGTH: 14
<212> TYPE: PRT
<213> ORGANISM: Limonium latifolium
<220> FEATURE:
<221> NAME/KEY: MISC_FEATURE
<222> LOCATION: (11)..(11)
<223> OTHER INFORMATION: Residue 11 is unknown
<220> FEATURE:
<221> NAME/KEY: UNSURE
<222> LOCATION: (2)..(4)
<223> OTHER INFORMATION: Residue 2-4 are alternate possibilities arising
      from ambiguities in sequencing.

<400> SEQUENCE: 8

Arg His Ala Gln Ile Asn Phe Asp Leu Pro Xaa Val Val Ala
1               5                   10
```

```
<210> SEQ ID NO 9
<211> LENGTH: 15
<212> TYPE: PRT
<213> ORGANISM: Limonium latifolium

<400> SEQUENCE: 9

His Arg Thr Glu Glu Glu Phe Ile Glu Leu Gly Leu Ser Ala Gly
1               5                   10                  15

<210> SEQ ID NO 10
<211> LENGTH: 9
<212> TYPE: PRT
<213> ORGANISM: Limonium latifolium

<400> SEQUENCE: 10

Glu Tyr Arg Gln Leu Gly Leu Leu Ala
1               5

<210> SEQ ID NO 11
<211> LENGTH: 11
<212> TYPE: PRT
<213> ORGANISM: Limonium latifolium

<400> SEQUENCE: 11

His Arg Thr Glu Glu Gln Phe Lys Gln Leu Gly
1               5                   10

<210> SEQ ID NO 12
<211> LENGTH: 23
<212> TYPE: DNA
<213> ORGANISM: Limonium latifolium
<220> FEATURE:
<221> NAME/KEY: misc_feature
<222> LOCATION: (6)..(6)
<223> OTHER INFORMATION: nucleotide N at position 6 is inosine
<220> FEATURE:
<221> NAME/KEY: misc_feature
<222> LOCATION: (3)..(3)
<223> OTHER INFORMATION: nucleotide Y at position 3 is either C or T
<220> FEATURE:
<221> NAME/KEY: misc_feature
<222> LOCATION: (4)..(4)
<223> OTHER INFORMATION: nucleotide M at position 4 is either A or C
<220> FEATURE:
<221> NAME/KEY: misc_feature
<222> LOCATION: (9)..(9)
<223> OTHER INFORMATION: nucleotide Y at position 9 is either C or T
<220> FEATURE:
<221> NAME/KEY: misc_feature
<222> LOCATION: (12)..(12)
<223> OTHER INFORMATION: nucleotide R at position 12 is either G or A
<220> FEATURE:
<221> NAME/KEY: misc_feature
<222> LOCATION: (15)..(15)
<223> OTHER INFORMATION: nucleotide R at position 15 is either G or A
<220> FEATURE:
<221> NAME/KEY: misc_feature
<222> LOCATION: (18)..(18)
<223> OTHER INFORMATION: nucleotide R at position 18 is either G or A
<220> FEATURE:
<221> NAME/KEY: misc_feature
<222> LOCATION: (21)..(21)
<223> OTHER INFORMATION: nucleotide Y at position 21 is either C or T
<220> FEATURE:
<221> NAME/KEY: misc_feature
<222> LOCATION: (22)..(22)
<223> OTHER INFORMATION: nucleotide M at position 22 is either A or C

<400> SEQUENCE: 12
caymgnacyg argargarta ymg                                    23
```

```
<210> SEQ ID NO 13
<211> LENGTH: 20
<212> TYPE: DNA
<213> ORGANISM: Limonium latifolium
<220> FEATURE:
<221> NAME/KEY: misc_feature
<222> LOCATION: (3)..(3)
<223> OTHER INFORMATION: nucleotide N at position 3 is inosine
<220> FEATURE:
<221> NAME/KEY: misc_feature
<222> LOCATION: (5)..(5)
<223> OTHER INFORMATION: nucleotide K at position 5 is either G or T
<220> FEATURE:
<221> NAME/KEY: misc_feature
<222> LOCATION: (6)..(6)
<223> OTHER INFORMATION: nucleotide R at position 6 is either G or A
<220> FEATURE:
<221> NAME/KEY: misc_feature
<222> LOCATION: (9)..(9)
<223> OTHER INFORMATION: nucleotide Y at position 9 is either C or T
<220> FEATURE:
<221> NAME/KEY: misc_feature
<222> LOCATION: (12)..(12)
<223> OTHER INFORMATION: nucleotide Y at position 12 is either C or T
<220> FEATURE:
<221> NAME/KEY: misc_feature
<222> LOCATION: (18)..(18)
<223> OTHER INFORMATION: nucleotide N at position 18 is inosine
<220> FEATURE:
<221> NAME/KEY: misc_feature
<222> LOCATION: (15)..(15)
<223> OTHER INFORMATION: nucleotide Y at position 15 is either C or T

<400> SEQUENCE: 13
tgnckrtayt cytcytcngt                                              20

<210> SEQ ID NO 14
<211> LENGTH: 23
<212> TYPE: DNA
<213> ORGANISM: Limonium latifolium
<220> FEATURE:
<221> NAME/KEY: misc_feature
<222> LOCATION: (3)..(3)
<223> OTHER INFORMATION: nucleotide N at position 3 is inosine
<220> FEATURE:
<221> NAME/KEY: misc_feature
<222> LOCATION: (9)..(9)
<223> OTHER INFORMATION: nucleotide Y at position 9 is either C or T
<220> FEATURE:
<221> NAME/KEY: misc_feature
<222> LOCATION: (6)..(6)
<223> OTHER INFORMATION: nucleotide Y at position 6 is either C or T
<220> FEATURE:
<221> NAME/KEY: misc_feature
<222> LOCATION: (12)..(12)
<223> OTHER INFORMATION: nucleotide N at position 12 is inosine
<220> FEATURE:
<221> NAME/KEY: misc_feature
<222> LOCATION: (15)..(15)
<223> OTHER INFORMATION: nucleotide Y at position 15 is either C or T
<220> FEATURE:
<221> NAME/KEY: misc_feature
<222> LOCATION: (18)..(18)
<223> OTHER INFORMATION: nucleotide R at position 18 is either G or A
<220> FEATURE:
<221> NAME/KEY: misc_feature
<222> LOCATION: (21)..(21)
<223> OTHER INFORMATION: nucleotide N at position 21 is inosine

<400> SEQUENCE: 14
ggntaygayg gnttygargg ngt                                          23
```

<210> SEQ ID NO 15
<211> LENGTH: 20
<212> TYPE: DNA
<213> ORGANISM: Limonium latifolium
<220> FEATURE:
<221> NAME/KEY: misc_feature
<222> LOCATION: (3)..(3)
<223> OTHER INFORMATION: nucleotide N at position 3 is inosine
<220> FEATURE:
<221> NAME/KEY: misc_feature
<222> LOCATION: (6)..(6)
<223> OTHER INFORMATION: nucleotide N at position 6 is inosine
<220> FEATURE:
<221> NAME/KEY: misc_feature
<222> LOCATION: (15)..(15)
<223> OTHER INFORMATION: nucleotide N at position 15 is any nucleotide
     (A, G, C or T)
<220> FEATURE:
<221> NAME/KEY: misc_feature
<222> LOCATION: (18)..(18)
<223> OTHER INFORMATION: nucleotide R at position 18 is either G or A
<220> FEATURE:
<221> NAME/KEY: misc_feature
<222> LOCATION: (9)..(9)
<223> OTHER INFORMATION: nucleotide Y at position 9 is C or T
<220> FEATURE:
<221> NAME/KEY: misc_feature
<222> LOCATION: (12)..(12)
<223> OTHER INFORMATION: nucleotide R at position 12 is either G or A

<400> SEQUENCE: 15
ttnacnccyt craanccrtc                                              20

<210> SEQ ID NO 16
<211> LENGTH: 22
<212> TYPE: DNA
<213> ORGANISM: Limonium latifolium
<220> FEATURE:
<221> NAME/KEY: misc_feature
<222> LOCATION: (3)..(3)
<223> OTHER INFORMATION: nucleotide H at position 3 is a nucleotide
     other than G (A, C, or T).
<220> FEATURE:
<221> NAME/KEY: misc_feature
<222> LOCATION: (6)..(6)
<223> OTHER INFORMATION: nucleotide Y at position 6 is either C or T.
<220> FEATURE:
<221> NAME/KEY: misc_feature
<222> LOCATION: (9)..(9)
<223> OTHER INFORMATION: nucleotide N at position 9 is inosine
<220> FEATURE:
<221> NAME/KEY: misc_feature
<222> LOCATION: (12)..(12)
<223> OTHER INFORMATION: nucleotide Y at position 12 is either C or T.
<220> FEATURE:
<221> NAME/KEY: misc_feature
<222> LOCATION: (15)..(15)
<223> OTHER INFORMATION: nucleotide Y at position 15 is either C or T.
<220> FEATURE:
<221> NAME/KEY: misc_feature
<222> LOCATION: (18)..(18)
<223> OTHER INFORMATION: nucleotide Y at position 18 is either C or T.
<220> FEATURE:
<221> NAME/KEY: misc_feature
<222> LOCATION: (21)..(21)
<223> OTHER INFORMATION: nucleotide Y at position 21 is either C or T.

<400> SEQUENCE: 16
atncaygtng aytayttytt yc                                           22

<210> SEQ ID NO 17
<211> LENGTH: 23
<212> TYPE: DNA
<213> ORGANISM: Limonium latifolium

```
<220> FEATURE:
<221> NAME/KEY: misc_feature
<222> LOCATION: (3)..(3)
<223> OTHER INFORMATION: nucleotide N at position 3 is inosine.
<220> FEATURE:
<221> NAME/KEY: misc_feature
<222> LOCATION: (6)..(6)
<223> OTHER INFORMATION: nucleotide R at position 6 is either G or A.
<220> FEATURE:
<221> NAME/KEY: misc_feature
<222> LOCATION: (9)..(9)
<223> OTHER INFORMATION: nucleotide R at position 9 is either G or A.
<220> FEATURE:
<221> NAME/KEY: misc_feature
<222> LOCATION: (12)..(12)
<223> OTHER INFORMATION: nucleotide R at position 12 is either G or A.
<220> FEATURE:
<221> NAME/KEY: misc_feature
<222> LOCATION: (15)..(15)
<223> OTHER INFORMATION: nucleotide R at position 15 is either G or A.
<220> FEATURE:
<221> NAME/KEY: misc_feature
<222> LOCATION: (21)..(21)
<223> OTHER INFORMATION: nucleotide R at position 21 is either G or A.
<220> FEATURE:
<221> NAME/KEY: misc_feature
<222> LOCATION: (18)..(18)
<223> OTHER INFORMATION: nucleotide N at position 18 is inosine.

<400> SEQUENCE: 17
acnggraara artartcnac rtg                                            23

<210> SEQ ID NO 18
<211> LENGTH: 19
<212> TYPE: DNA
<213> ORGANISM: Limonium latifolium

<400> SEQUENCE: 18
ccaccaacat ctaccaatg                                                 19

<210> SEQ ID NO 19
<211> LENGTH: 20
<212> TYPE: DNA
<213> ORGANISM: Limonium latifolium
<220> FEATURE:
<221> NAME/KEY: misc_feature
<222> LOCATION: (3)..(3)
<223> OTHER INFORMATION: nucleotide at position 3 is inosine
<220> FEATURE:
<221> NAME/KEY: misc_feature
<222> LOCATION: (6)..(6)
<223> OTHER INFORMATION: nucleotide N at position 6 is any nucleotide
      (A, G, C or T).
<220> FEATURE:
<221> NAME/KEY: misc_feature
<222> LOCATION: (9)..(9)
<223> OTHER INFORMATION: nucleotide H at position 9 is any nucleotide
      not G (A, C or T).
<220> FEATURE:
<221> NAME/KEY: misc_feature
<222> LOCATION: (12)..(12)
<223> OTHER INFORMATION: nucleotide N t position 12 is inosine
<220> FEATURE:
<221> NAME/KEY: misc_feature
<222> LOCATION: (12)..(12)
<223> OTHER INFORMATION: nucleotide N at position 12 is inosine
<220> FEATURE:
<221> NAME/KEY: misc_feature
<222> LOCATION: (10)..(10)
<223> OTHER INFORMATION: nucleotide Y at position 10 is either C or T.
<220> FEATURE:
<221> NAME/KEY: misc_feature
<222> LOCATION: (15)..(15)
<223> OTHER INFORMATION: nucleotide Y at position 15 is either C or T.
```

-continued

```
<220> FEATURE:
<221> NAME/KEY: misc_feature
<222> LOCATION: (18)..(18)
<223> OTHER INFORMATION: nucleotide N at position 18 is inosine
<220> FEATURE:
<221> NAME/KEY: misc_feature
<222> LOCATION: (19)..(19)
<223> OTHER INFORMATION: nucleotide W at position 19 is wyosine

<400> SEQUENCE: 19
acngcnatny tngaygcnns                                               20

<210> SEQ ID NO 20
<211> LENGTH: 500
<212> TYPE: DNA
<213> ORGANISM: Limonium latifolium

<400> SEQUENCE: 20
gggtatgacg ggtttgaggg ggtaaaaaca ttggtagatg ttggtgggag ttcaggggat     60
tgtttgagga tgattataaa caagtataag gatattccaa aagccattaa ctttgattta   120
cctgaggttg tggcgaaagc gcctaagatc ccaggtatta cccatgtggg aggaaacacg   180
ttcgaatcgg ttccttcggg tgatgctata tttgtgaagt gggtgctgac gtgtttcaca   240
gatgaagagg tgatcacact tatgcgcaac tgtaacaagg cgttgccagt gggaggaaaa   300
ctgatatgct cagaacccac gttgcctgaa aactcggatg aaagtcatag gactcgtgct   360
ttgcttgtag ccgacatctt tatcatgact acttacaggg caaagggaaa gcacaggaca   420
gaggaagagt acagacaact cggtctctta gccggattcc ccaaattccg agttatccac   480
gtcgactact ttttccccgt                                               500

<210> SEQ ID NO 21
<211> LENGTH: 573
<212> TYPE: DNA
<213> ORGANISM: Limonium latifolium

<400> SEQUENCE: 21
ccaccaacat ctaccaatgt tcctatgtcc cttactgcca tcgtccgcct gaaggtgcct     60
gaggctatct ggtctaatgg ttccaacacc ccggtctctg ccgctgagat cctcagtcgt   120
cttcctgatg ccccacctac cgccgatgcg gagaatctcc agcgtcttct ccgtgtactg   180
actagttttg gcgttttctc ggaacacctt gacaccacca gttctagttc atcatctact   240
tcggaacgga ggtactgttt gacggaggta ggacagaccc tggtatcatt tgatgagagc   300
tgtccatctc acggtgcata cgttctacaa caccaccagg agacgctttt gaaagcttgg   360
ccatttcttc acacagcaat tctagatgcg agcactgagc catttgcaag ggtgaatggt   420
gagccagctt accagtacta cgggaagaat gacgagttga caagaatat gcagtatgct   480 atgtcagggg tatcagtgcc ttatatgaaa gccttgttag aagtgggta cgatgggttt   540 gagggagtaa aaacattggt agatgttggt gga                                573

<210> SEQ ID NO 22
<211> LENGTH: 663
<212> TYPE: DNA
<213> ORGANISM: Limonium latifolium

<400> SEQUENCE: 22
gtgctaagcc agacacacac acgcagagtg agtgagtcag tcaattggtg atagacagtt     60
ccagttccag tcccagttat caccaaccaa ccaaccaagc aagcaaccaa gcgagaaaaa   120
```

```
tggcgaacca ctcctcagct gcagccatgg tggtcgacga gacttcagag gcccgaaaca    180
atgcgaggct aaagatcatc gaactcgcga acttaatcag tgttcctatg tcccttactg    240
ccatcgtccg cctgaaggtg cctgaggcta tctggtctaa tggttccaac accccggtct    300
ctgccgctga gatcctcagt cgtcttcctg atgccccgc taccgccgat gcggagaatc     360
tccagcgtct tctccgtgta ctgactagtt ttggcgtttt ctcggaacac cttgacacca    420
ccagttctag ttcatcatct acttcggaac ggaggtactg tttgacgag gtaggacaga    480 ccctggtatc atttgatgag agctgtccat ctcacggtgc atacgttcta caacaccacc    540
aggagacgct tttgaaagct tggccatttc ttcacacagc aattctagac gcgagtactg    600
agccatttgc aagggtgaat ggtgagccag cttaccagta ctacgggaag aatgacgagt    660
tga                                                                   663

<210> SEQ ID NO 23
<211> LENGTH: 26
<212> TYPE: DNA
<213> ORGANISM: Limonium latifolium

<400> SEQUENCE: 23
tcaactcgtc attcttcccg tactac                                          26

<210> SEQ ID NO 24
<211> LENGTH: 804
<212> TYPE: DNA
<213> ORGANISM: Limonium latifolium

<400> SEQUENCE: 24
gagacgcttt tgaaagcttg gccatttctt cacacagcaa ttctagacgc gagtactgag     60
ccatttgcaa gggtgaatgg tgagccagct taccagtact acgggaagaa tgacgagttg    120
aacaagaata tgcagtatgc tatgtcaggg gtatcagtgc cttatatgaa agccttgtta    180
ggaagtgggt acgatgggtt tgaggagta aaaacattgg tagatgttgg tgggagttca    240
ggggattgtt tgaggatgat tataaacaag tataaggata ttccaaaagc cattaacttt    300
gatttacctg aggttgtggc gaaagcgcct aagatcccag gtattaccca tgtgggagga    360
aacatgttcg aatcggttcc ttcgggtgat gctatatttg tgaagtgggt gctgacgtgt    420
ttcacagatg aagaggtgat cacacttatg cgcaactgta caaggcgtt gccagtggga    480 ggaaaactaa tatgctcaga acccacgttg cctgaaaact cggatgaaag tcataggact    540
cgtgctttgc ttgtagccga catctttatc atgactactt acaggggcaa gggaaagcac    600
aggacagagg aagaatacag acaactcggt ctcttagccg gattcccaa attccgagtt     660 atccatgtcg actatttctt ccccgtggta gagttccaga agtgaatatc tgccatcatg    720
atcatgaggc ccgtccgccc gcccaactat ctcttttta atttcttttt cctttttcttt    780 tttttttctg tttctgtgtt accc                                            804

<210> SEQ ID NO 25
<211> LENGTH: 687
<212> TYPE: DNA
<213> ORGANISM: Limonium latifolium

<400> SEQUENCE: 25
cgggcttacc agtactacgg gaagaatgac gagttgaaca agaatatgca gtatgctatg     60 tcagggtat cagtgcctta tatgaaagcc ttgttaggaa gtgggtacga tgggtttgag    120
ggagtaaaaa cattggtaga tgttggtggg agttcagggg attgtttgag gatgattata    180
```

-continued

```
aacaagtata aggatattcc aaaagccatt aactttgatt tacctgaggt tgtggcgaaa      240
gcgcctaaga tcccaggtat tacacatgtg ggaggaaaca tgttcgaatc ggttccttcg      300
ggtgatgcta tatttgtgaa gtgggtgctg acgtgtttca cagatgaaga ggtgatcaca      360
cttatgcgca actgtaacaa ggcattgcca gtgggaggaa aactaatatg ctcagaaccc      420
acgttgcctg aaaactcgga cgaaagtcat aggactcgtg ctttgcttgt agccgacatc      480
tttatcatga ctacttacag ggcaaaggga agcacagga cagaggaaga gtacagacaa       540
ctcggtctct tagccggatt ccccaaattc cgagttatcc atgtcgacta tttcttcccc      600
gtggtagagt tccagaagtg aatgtccatc atcatcatga ggcccgcccg cccgcccgcc      660
cgactatctc tttttattat tttttt                                           687
```

<210> SEQ ID NO 26
<211> LENGTH: 813
<212> TYPE: DNA
<213> ORGANISM: Limonium latifolium

<400> SEQUENCE: 26

```
aaaaacattg gtagatgttg gtgggagttc agggattgt ttgaggatga ttataaacaa         60
gtataaggat attccaaaag ccattaactt tgatttacct gaggttgtgg cgaaagcgcc       120
taagatccca ggtattacac atgtgggagg aaacatgttc gaatcggttc cttcgggtga      180
tgctatattt gtgaagtggg tgctgacgtg tttcacagat gaagaggtga tcacacttat      240
gcgcaactgt aacaaggcat tgccagtggg aggaaaacta atatgctcag aacccacgtt      300
gcctgaaaac tcggacgaaa gtcataggac tcgtgctttg cttgtagccg acatctttat      360
catgactact acagggcaa agggaaagca caggacagag gaagagtaca gacaactcgg       420
tctcttagcc ggattcccca aattccgagt tatccatgtc gactatttct ccccgtggt       480 agagttccag aagtgaatgt ccatcatcat catgaggccc gccgccgc cgcccgact       540 atctcttttt attattttt tgtgtttgt gtgtgtctgt ctgtccgtct gtttaatttt       600
aatttgggat caggttataa ataatttct cagttgatga tttggattgg ctgttgttg      660 ttgtactgag catatataaa cccaatccat cctaagagga gtgaaattga gtcgtcgtac      720
gtactcgtat catttcatgg cggaccgaat gtatggggtc actaataaat aaaaatttct      780
atagttaatt tttcatgaaa aaaaccggga att                                  813
```

<210> SEQ ID NO 27
<211> LENGTH: 736
<212> TYPE: DNA
<213> ORGANISM: Limonium latifolium

<400> SEQUENCE: 27

```
agcacgggac aacccgctct cgccacggga gcagctcaag cagttcaccg acagccaacg       60
ggtttgaggg agtaaaaaca ttggtagatg ttggtgggag ttcaggggat tgtttgagga      120
tgattataaa caagtataag gatattccaa aagccattaa ctttgattta cctgaggttg      180
tggcgaaagc gcctaagatc ccaggtatta cacatgtggg aggaaacatg ttcgaatcgg      240
ttccttcggg tgatgctata tttgtgaagt gggtgctgac gtgtttcaca gatgaagagg      300
tgatcacact tatgcgcaac tgtaacaagg cattgccagt gggaggaaaa ctaatatgct      360
cagaacccac gttgcctgaa aactcggacg aaagtcatag gactcgtgct ttgcttgtag      420
ccgacatctt tatcatgact acttacaggg caaagggaaa gcacaggaca gaggaagagt      480
acagacaact cggtctctta gccggattcc ccaaattccg agttatccat gtcgactatt      540
```

```
tcttccccgt ggtagagttc cagaagtgaa tgtccatcat catcatgagg cccgcccgcc      600
cgcccgcccg actatctctt tttattattt tttttgtgtt tgtgtgtgtc tgtctgtccg      660 tctgttttaat tttaatttgg gatcaggtta taaataattt ctcagttga tgattaaaaa      720 aaaaaaaaaa aaaaaa                                                      736

<210> SEQ ID NO 28
<211> LENGTH: 1414
<212> TYPE: DNA
<213> ORGANISM: Limonium latifolium

<400> SEQUENCE: 28
gtgctaagcc agacacacac acgcagagtg agtgagtcag tcaattggtg atagacagtt       60
ccagttccag tcccagttat caccaaccaa ccaaccaagc aagcaaccaa gcgagaaaaa      120
tggcgaacca ctcctcagct gcagccatgg tggtcgacga gacttcagag gcccgaaaca      180
atgcgaggct aaagatcatc gaactcgcga acttaatcag tgttcctatg tcccttactg      240
ccatcgtccg cctgaaggtg cctgaggcta tctggtctaa tggttccaac accccggtct      300
ctgccgctga gatcctcagt cgtcttcctg atgcccccgc taccgccgat gcggagaatc      360
tccagcgtct tctccgtgta ctgactagtt ttggcgtttt ctcggaacac cttgacacca      420
ccagttctag ttcatcatct acttcggaac ggaggtactg tttgacgag gtaggacaga       480 ccctggtatc atttgatgag agctgtccat ctcacggtgc atacgttcta caacaccacc      540
aggagacgct tttgaaagct tggccatttc ttcacacagc aattctagac gcgagtactg      600
agccatttgc aagggtgaat ggtgagccag cttaccagta ctacgggaag aatgacgagt      660
tgaacaagaa tatgcagtat gctatgtcag gggtatcagt gccttatatg aaagcccttgt     720 taggaagtgg gtacgatggg tttgagggag taaaaacatt ggtagatgtt ggtgggagtt      780
caggggattg tttgaggatg attataaaca agtataagga tattccaaaa gccattaact      840
ttgatttacc tgaggttgtg gcgaaagcgc ctaagatccc aggtattacc catgtgggag      900
gaaacatgtt cgaatcggtt ccttcgggtg atgctatatt tgtgaagtgg gtgctgacgt      960
gtttcacaga tgaagaggtg atcacactta tgcgcaactg taacaaggcg ttgccagtgg     1020 gaggaaaaact aatatgctca gaaccacgt tgcctgaaaa ctcggatgaa agtcatagga      1080 ctcgtgctt gcttgtagcc gacatctta tcatgactac ttacagggca agggaaagc       1140 acaggacaga ggaagaatac agacaactcg gtctcttagc cggattcccc aaattccgag     1200
ttatccatgt cgactatttc ttccccgtgg tagagttcca gaagtgaatg tccatcatca     1260
tcatgaggcc cgcccgccg cccgcccgac tatctctttt tattatttt tttgtgttg       1320 tgtgtgtctg tctgtccgtc tgtttaattt taatttggga tcaggttata ataatttttc    1380
tcagttgatg attaaaaaaa aaaaaaaaa aaaa                                  1414

<210> SEQ ID NO 29
<211> LENGTH: 375
<212> TYPE: PRT
<213> ORGANISM: Limonium latifolium

<400> SEQUENCE: 29

Met Ala Asn His Ser Ser Ala Ala Ala Met Val Val Asp Glu Thr Ser
1               5                   10                  15

Glu Ala Arg Asn Asn Ala Arg Leu Lys Ile Ile Glu Leu Ala Asn Leu
            20                  25                  30
```

```
Ile Ser Val Pro Met Ser Leu Thr Ala Ile Val Arg Leu Lys Val Pro
        35                  40                  45
Glu Ala Ile Trp Ser Asn Gly Ser Asn Thr Pro Val Ser Ala Ala Glu
 50                  55                  60
Ile Leu Ser Arg Leu Pro Asp Ala Pro Ala Thr Ala Asp Ala Glu Asn
 65                  70                  75                  80
Leu Gln Arg Leu Leu Arg Val Leu Thr Ser Phe Gly Val Phe Ser Glu
                 85                  90                  95
His Leu Asp Thr Thr Ser Ser Ser Ser Ser Thr Ser Glu Arg Arg
                100                 105                 110
Tyr Cys Leu Thr Glu Val Gly Gln Thr Leu Val Ser Phe Asp Glu Ser
                115                 120                 125
Cys Pro Ser His Gly Ala Tyr Val Leu Gln His Gln Glu Thr Leu
        130                 135                 140
Leu Lys Ala Trp Pro Phe Leu His Thr Ala Ile Leu Asp Ala Ser Thr
145                 150                 155                 160
Glu Pro Phe Ala Arg Val Asn Gly Glu Pro Ala Tyr Gln Tyr Tyr Gly
                165                 170                 175
Lys Asn Asp Glu Leu Asn Lys Asn Met Gln Tyr Ala Met Ser Gly Val
                180                 185                 190
Ser Val Pro Tyr Met Lys Ala Leu Leu Gly Ser Gly Tyr Asp Gly Phe
                195                 200                 205
Glu Gly Val Lys Thr Leu Val Asp Val Gly Gly Ser Ser Gly Asp Cys
        210                 215                 220
Leu Arg Met Ile Ile Asn Lys Tyr Lys Asp Ile Pro Lys Ala Ile Asn
225                 230                 235                 240
Phe Asp Leu Pro Glu Val Val Ala Lys Ala Pro Lys Ile Pro Gly Ile
                245                 250                 255
Thr His Val Gly Gly Asn Met Phe Glu Ser Val Pro Ser Gly Asp Ala
        260                 265                 270
Ile Phe Val Lys Trp Val Leu Thr Cys Phe Thr Asp Glu Glu Val Ile
        275                 280                 285
Thr Leu Met Arg Asn Cys Asn Lys Ala Leu Pro Val Gly Gly Lys Leu
        290                 295                 300
Ile Cys Ser Glu Pro Thr Leu Pro Glu Asn Ser Asp Glu Ser His Arg
305                 310                 315                 320
Thr Arg Ala Leu Leu Val Ala Asp Ile Phe Ile Met Thr Thr Tyr Arg
                325                 330                 335
Ala Lys Gly Lys His Arg Thr Glu Glu Tyr Arg Gln Leu Gly Leu
        340                 345                 350
Leu Ala Gly Phe Pro Lys Phe Arg Val Ile His Val Asp Tyr Phe Phe
        355                 360                 365
Pro Val Val Glu Phe Gln Lys
        370                 375
```

<210> SEQ ID NO 30
<211> LENGTH: 31
<212> TYPE: DNA
<213> ORGANISM: Limonium latifolium

<400> SEQUENCE: 30
gcggatccaa tggcgaacca ctcctcagct g      31

```
<210> SEQ ID NO 31
<211> LENGTH: 29
<212> TYPE: DNA
<213> ORGANISM: Limonium latifolium

<400> SEQUENCE: 31
ctcgagtcac ttctggaact ctaccacgg                                29
```